(12) United States Patent
Kinberger et al.

(10) Patent No.: US 7,713,944 B2
(45) Date of Patent: May 11, 2010

(54) OLIGOMERS COMPRISING ACTIVATED DISULFIDES WHICH BIND TO PLASMA PROTEINS AND THEIR USE FOR DELIVERY TO CELLS

(75) Inventors: Garth A. Kinberger, San Diego, CA (US); Martin A. Maier, Carlsbad, CA (US); Richard H. Griffey, Vista, CA (US); Eric E. Swayze, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 11/251,564

(22) Filed: Oct. 13, 2005

(65) Prior Publication Data

US 2006/0142232 A1 Jun. 29, 2006

Related U.S. Application Data

(60) Provisional application No. 60/618,882, filed on Oct. 13, 2004.

(51) Int. Cl.
*A61K 31/70* (2006.01)
*C07H 21/04* (2006.01)
*A61K 38/00* (2006.01)

(52) U.S. Cl. ........................ 514/44; 536/23.1; 536/24.5; 530/300

(58) Field of Classification Search ........................ None
See application file for complete search history.

(56) References Cited

U.S. PATENT DOCUMENTS

| | | | |
|---|---|---|---|
| 5,612,034 A | * | 3/1997 | Pouletty et al. .......... 424/184.1 |
| 6,153,737 A | * | 11/2000 | Manoharan et al. ........ 536/22.1 |
| 2003/0104985 A1 | * | 6/2003 | Matulic-Adamic et al. ..... 514/7 |
| 2003/0166512 A1 | | 9/2003 | Xie |
| 2004/0147027 A1 | * | 7/2004 | Troy et al. ................. 435/458 |
| 2005/0107325 A1 | * | 5/2005 | Manoharan et al. ........... 514/44 |

OTHER PUBLICATIONS

Kratz, F. et al., "Probing the Cysteine-34 Position of Endogenous Serum Albumin with Thiol-Binding Doxorubicin Derivatives, Improved Efficacy of an Acid-Sensitive Doxorubicin Derivative with Specific Albumin-Binding Properties Compared to That of the Parent Compound," *J. Med. Chem.* (2002) 45(25):5523-5533.
Lavigne, C. et al., "Cationic Liposomes/Lipids for Oligonucleotide Delivery: Application to the Inhibition of Tumorigenicity of Kaposi's Sarcoma by Vascular Endothelial Growth Factor Antisense Oligodeoxynucleotides," *Methods in Enzymology* (2004) 387:189-210.
Mansour, A. M. et al., "A New Approach for the Treatment of Malignant Melanoma: Enhanced Antitumor Efficacy of an Albumin-binding Doxorubicin Prodrug That Is Cleaved by Matrix Metalloproteinase 2," *Cancer Res.* (2003) 63:4062-4066.
Uhlmann, E. et al., "Antisense Oligonucleotides: A New Therapeutic Principle," *Chem. Rev.* (1990) 90(4):543-584.
Vivès, E. et al., "Selective Coupling of a Highly Basic Peptide to an Oligonucleotide," *Tetrahedron Lett.* (1997) 38(7):1183-1186.
Zuckermann, R. et al, "Efficient methods for attachment of thiol specific probes to the 3'-ends of synthetic oligodeoxyribonucleotides," *Nucleic Acids. Res.* (1987) 15(13):5305-5321.
Zuckermann, R. N. et al., "Site-Selective Cleavage of RNA by a Hybrid Enzyme," *J. Am. Chem. Soc.* (1988) 110(5):1614-1615.

* cited by examiner

*Primary Examiner*—Tracy Vivlemore
(74) *Attorney, Agent, or Firm*—Knobbe Martens Olson & Bear LLP

(57) ABSTRACT

The activated oligomer compounds described herein are capable of forming bio-reversible covalent bonds with plasma proteins, in particular with human serum albumin. The plasma protein-oligomer complexes of the present invention exhibit enhanced cellular entry and significantly enhanced serum half-life.

18 Claims, 8 Drawing Sheets

Figure 3
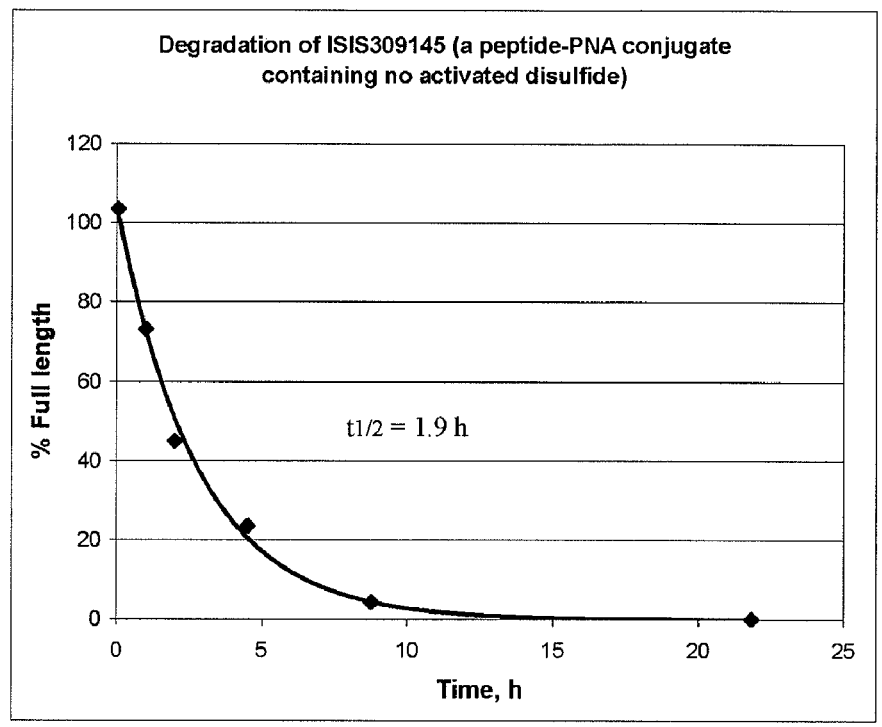
Figure 3a
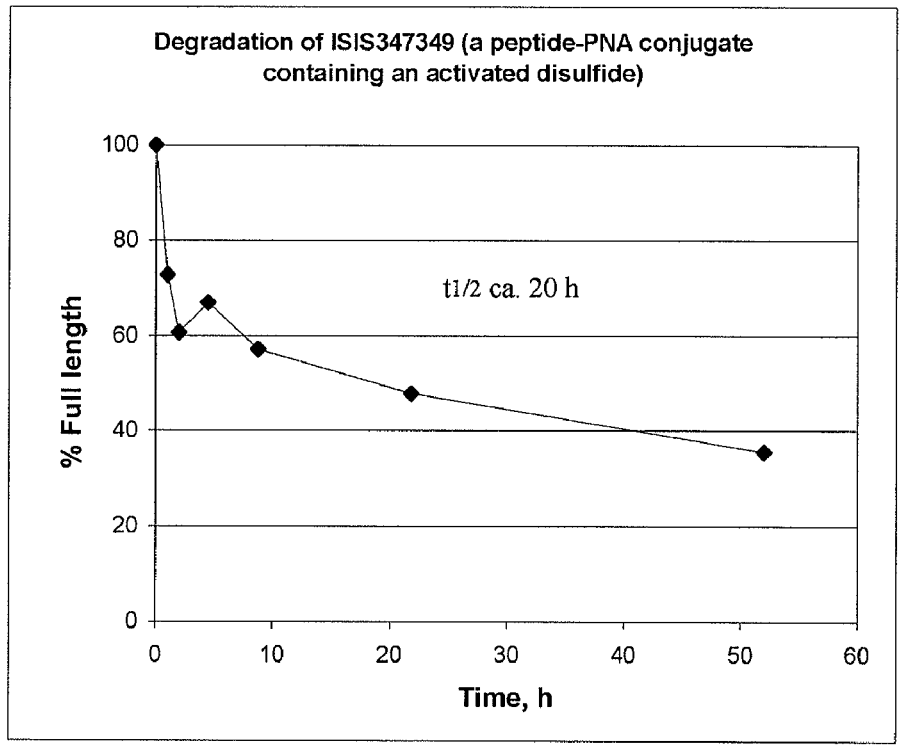
Figure 3b

Figure 4
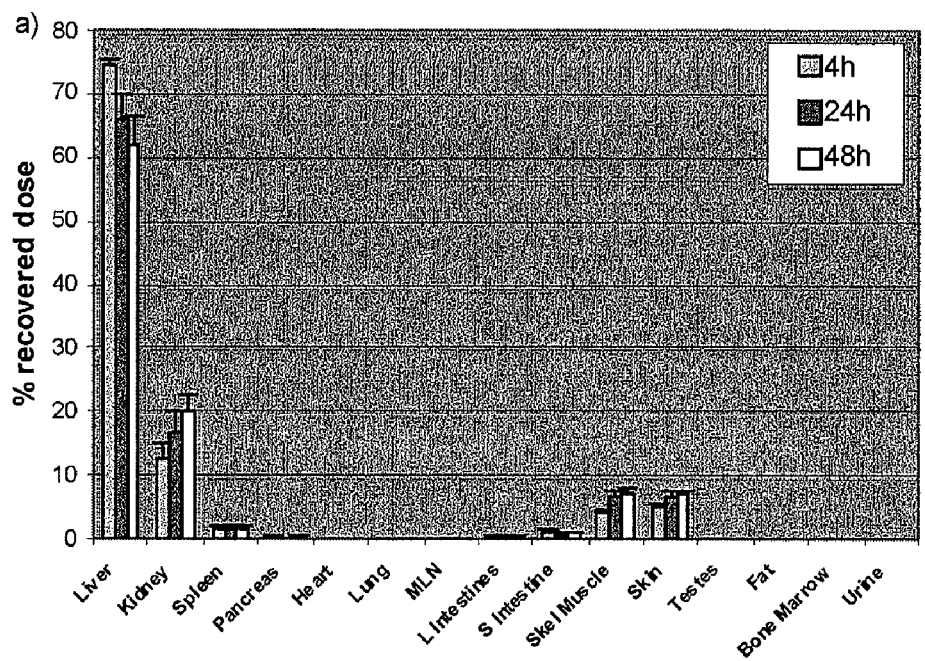
Figure 4a
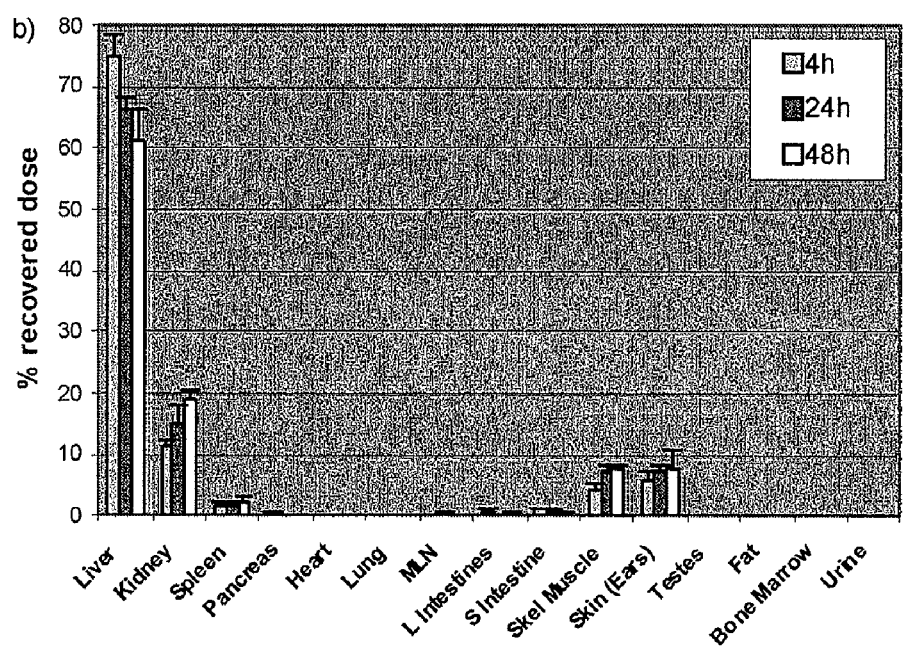
Figure 4b

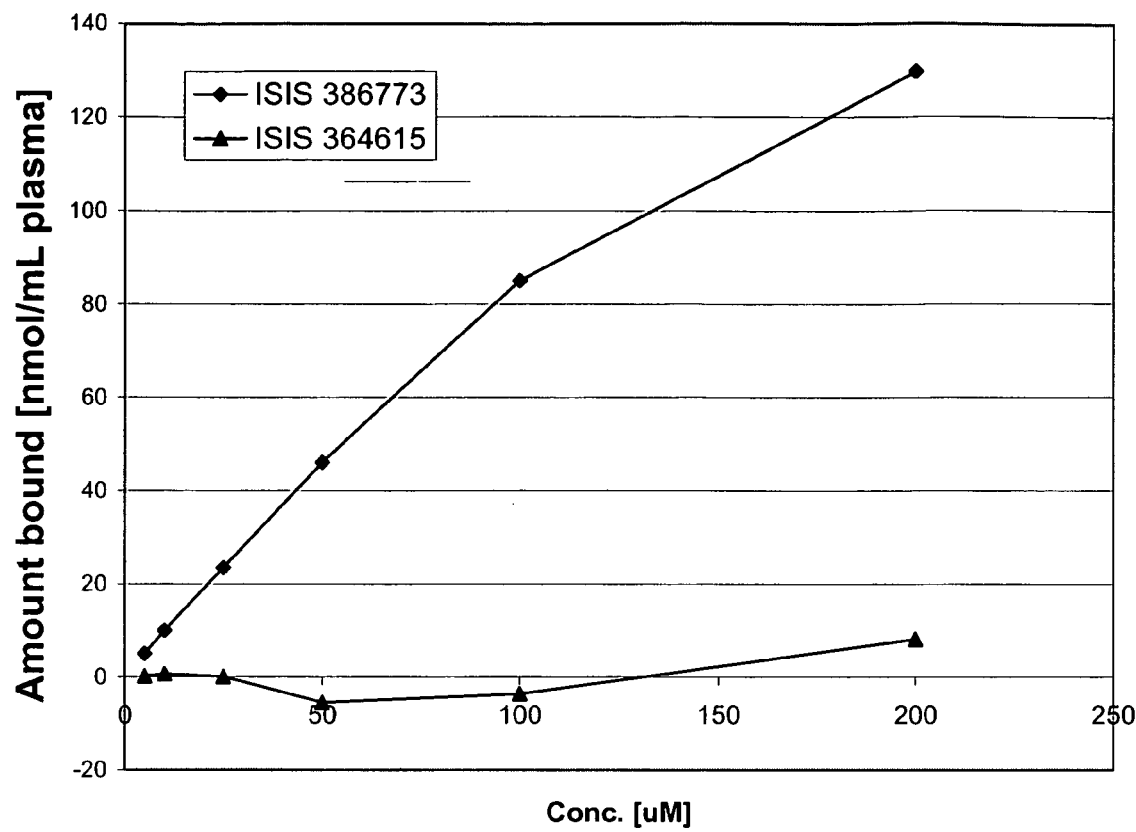
Figure 5: plasma protein binding capacity for ISIS 386773 and ISIS 364615 as a function of their plasma concentration.

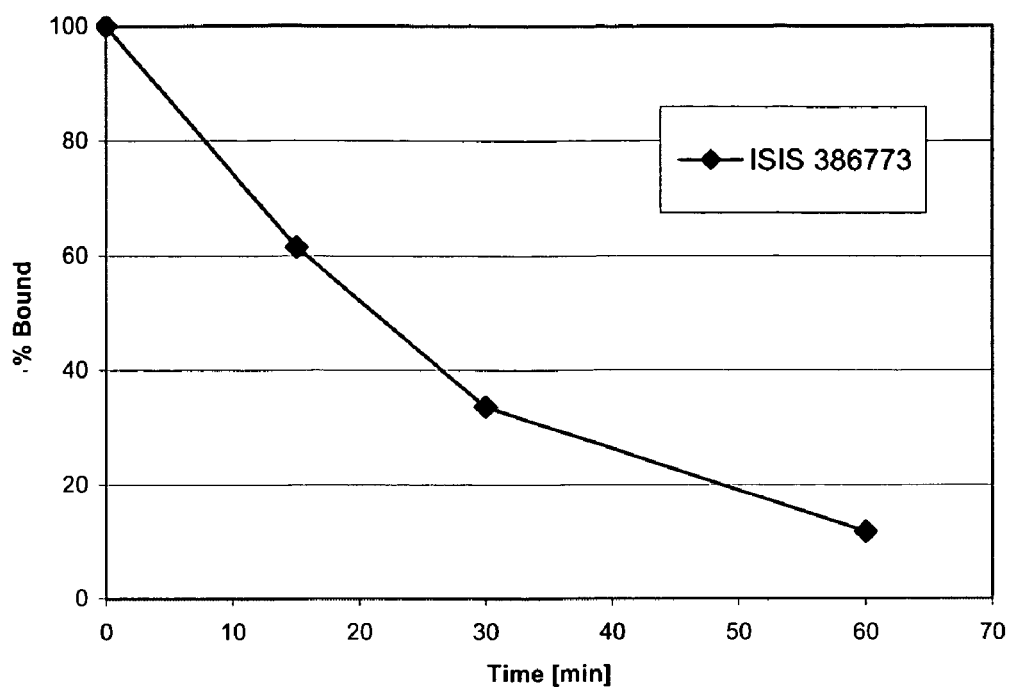
Figure 6. Release kinetics of ISIS 386773 from plasma proteins after the addition of GSH

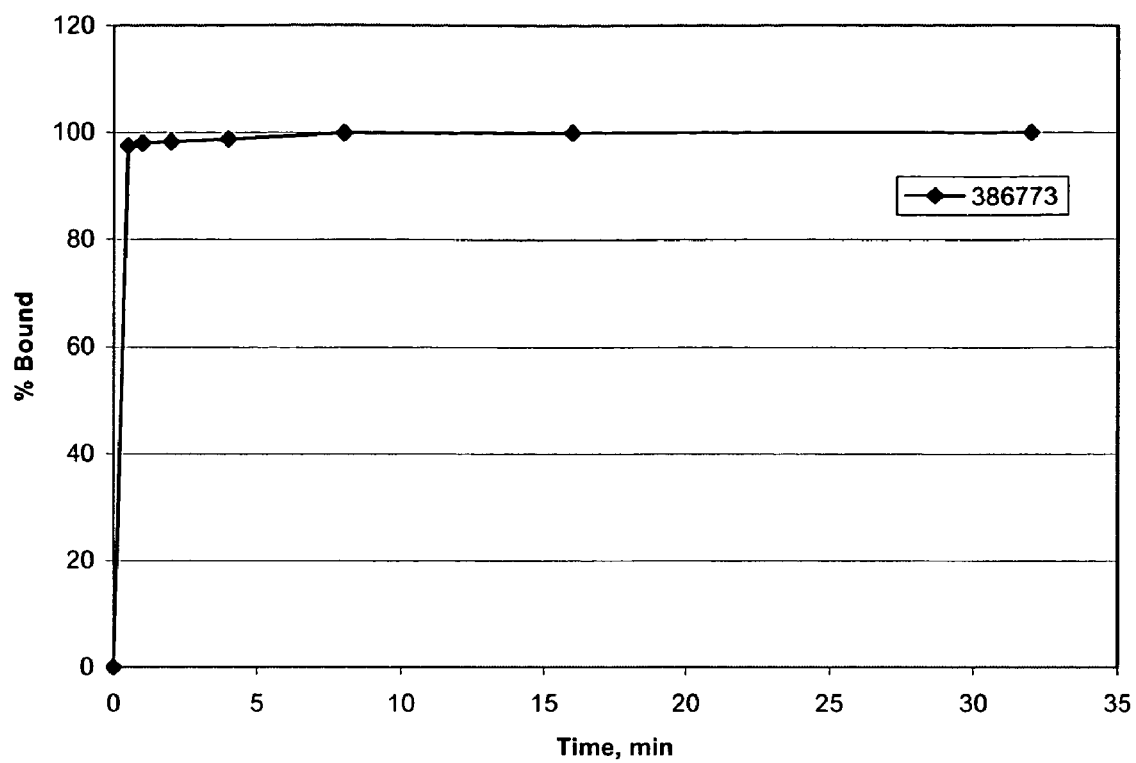
Figure 7. Kinetics of binding of ISIS 386773 to plasma proteins.

SEQUENCE LISTING

<160> NUMBER OF SEQ ID NOS: 12

<210> SEQ ID NO 1
<211> LENGTH: 19
<212> TYPE: RNA
<213> ORGANISM: Artificial Sequence
<220> FEATURE:
<223> OTHER INFORMATION: Synthetic Oligonucleotide Compound

<400> SEQUENCE: 1
cgagaggcgg acgggaccg                                              19

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide Compound

<400> SEQUENCE: 2
cgagaggcgg acgggaccgt t                                           21

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide Compound

<400> SEQUENCE: 3
cggtcccgtc cgcctctcgt t                                           21

<210> SEQ ID NO 4
<211> LENGTH: 15
<212> TYPE: DNA
<213> ORGANISM: Artificial Sequence
<220> FEATURE:
<223> OTHER INFORMATION: Synthetic Oligonucleotide Compound
<220> FEATURE:
<221> NAME/KEY: misc_feature
<222> LOCATION: 1
<223> OTHER INFORMATION: n = c linked to the peptide sequence Lys Lys
      Orn Lys Lys Orn Lys Lys
<220> FEATURE:
<221> NAME/KEY: misc_feature
<222> LOCATION: 15
<223> OTHER INFORMATION: n = g linked to Lys linked to a pyridyl
      disulfide containing molecule

<400> SEQUENCE: 4
nacagatgac attan                                                  15

<210> SEQ ID NO 5
<211> LENGTH: 15
<212> TYPE: DNA
<213> ORGANISM: Artificial Sequence
<220> FEATURE:
<223> OTHER INFORMATION: Synthetic Oligonucleotide Compound
<220> FEATURE:
<221> NAME/KEY: misc_feature
<222> LOCATION: 1
<223> OTHER INFORMATION: n = c linked to an octapeptide comprising
      D-Lys
<220> FEATURE:
<221> NAME/KEY: misc_feature
<222> LOCATION: 15
<223> OTHER INFORMATION: n = g linked to Lys linked to a pyridyl
      disulfide containing molecule

```
<400> SEQUENCE: 5
nacagatgac attan                                                        15

<210> SEQ ID NO 6
<211> LENGTH: 15
<212> TYPE: DNA
<213> ORGANISM: Artificial Sequence
<220> FEATURE:
<223> OTHER INFORMATION: Synthetic Oligonucleotide Compound
<220> FEATURE:
<221> NAME/KEY: misc_feature
<222> LOCATION: 1
<223> OTHER INFORMATION: n = c linked to an octapeptide comprising D-Lys
<220> FEATURE:
<221> NAME/KEY: misc_feature
<222> LOCATION: 15
<223> OTHER INFORMATION: n = g linked to Lys linked to a pyridyl
      disulfide containing molecule

<400> SEQUENCE: 6
nacagatgac attan                                                        15

<210> SEQ ID NO 7
<211> LENGTH: 15
<212> TYPE: DNA
<213> ORGANISM: Artificial Sequence
<220> FEATURE:
<223> OTHER INFORMATION: Synthetic Oligonucleotide Compound
<220> FEATURE:
<221> NAME/KEY: misc_feature
<222> LOCATION: 1
<223> OTHER INFORMATION: n - c linked to an octapeptide comprising D-Lys
      linked to a pyridyl disulfide containing molecule
<220> FEATURE:
<221> NAME/KEY: misc_feature
<222> LOCATION: 15
<223> OTHER INFORMATION: n = g linked to Lys

<400> SEQUENCE: 7
nacagatgac attan                                                        15

<210> SEQ ID NO 8
<211> LENGTH: 15
<212> TYPE: DNA
<213> ORGANISM: Artificial Sequence
<220> FEATURE:
<223> OTHER INFORMATION: Synthetic Oligonucleotide Compound
<220> FEATURE:
<221> NAME/KEY: misc_feature
<222> LOCATION: 1
<223> OTHER INFORMATION: n = c linked to a octapeptide comprising D-Lys
      linked to a pyridyl disulfide containing molecule
<220> FEATURE:
<221> NAME/KEY: misc_feature
<222> LOCATION: 15
<223> OTHER INFORMATION: n = g linked to Lys linked to a Biotin
      containing molecule

<400> SEQUENCE: 8
nacagatgac attan                                                        15

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide Compound

<400> SEQUENCE: 9
```

-continued

```
ctgctagcct ctggatttga                                          20

<210> SEQ ID NO 10
<211> LENGTH: 15
<212> TYPE: DNA
<213> ORGANISM: Artificial Sequence
<220> FEATURE:
<223> OTHER INFORMATION: Synthetic Oligonucleotide Compound
<220> FEATURE:
<221> NAME/KEY: misc_feature
<222> LOCATION: 1
<223> OTHER INFORMATION: n = c linked to an octopeptide comprising Lys
      linked to a pyridyl disulfide containing molecule
<220> FEATURE:
<221> NAME/KEY: misc_feature
<222> LOCATION: 15
<223> OTHER INFORMATION: n = G linked to Lys

<400> SEQUENCE: 10
nacagatgac attan                                               15

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide Compound

<400> SEQUENCE: 11
tgtctctggt ccttactt                                            18

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide Compound
<220> FEATURE:
<221> NAME/KEY: misc_feature
<222> LOCATION: 1
<223> OTHER INFORMATION: n = t linked to a pyridyl disulfide containing
      molecule

<400> SEQUENCE: 12
ngtctctggt ccttactt                                            18
```

OLIGOMERS COMPRISING ACTIVATED DISULFIDES WHICH BIND TO PLASMA PROTEINS AND THEIR USE FOR DELIVERY TO CELLS

RELATED APPLICATIONS

This application claims priority to U.S. Provisional Application Ser. No. 60/618,882 filed Oct. 13, 2004, which is incorporated herein in its entirety.

TECHNICAL FIELD

The present invention describes activated oligomeric compounds capable of forming covalent bonds with plasma proteins, in particular with human serum albumin; methods of treating a subject with the activated oligomeric compounds; and methods of synthesizing the activated oligomeric compounds.

BACKGROUND OF THE INVENTION

Recent reports in the literature describe the use of serum albumin for improved drug delivery by binding the drug to the protein through covalent linkages. Using albumin-based drug delivery, antiproliferative drugs, such as doxorubicin or methotrexate, have been shown to exhibit improved pharmacokinetic properties and antitumor activity. (See Stehle, G.; Wunder, A.; Sinn, H.; Schrenk, H. H.; Schutt, S.; Frei, E.; Hartung, G.; Maier-Borst, W.; Heene, D. L. (1997) Pharmacokinetics of methotrexate-albumin conjugates in tumor-bearing rats. *Anti-Cancer Drugs*, 8, 835-844; Stehle, G.; Wunder, A.; Schrenk, H. H.; Hartung, G.; Heene, D. L.; Sinn, H. (1999) Methotrexate-albumin conjugate causes tumor growth delay in Dunning R332 HI prostate cancer-bearing rats. *Anti-Cancer Drugs*, 10, 405-411; Mansour, A. M., Drevs, J. et al. (2003) A New Approach for the Treatment of Malignant Melanoma: Enhanced Antitumor Efficacy of an Albumin-binding Doxorubicin Prodrug That Is Cleaved by Matrix Metalloproteinase 2. *Cancer Research* 63, 4062-4066).

SUMMARY OF THE INVENTION

The present invention is directed to an activated oligomer which is capable of forming a bio-reversible bond with plasma proteins, i.e. the activated oligomer is bound to plasma proteins under plasma conditions, however become released under cellular conditions. The activated oligomers of the present invention comprise an oligomer and an activated disulfide moiety capable of forming bio-reversible bonds with plasma proteins. In another embodiment of the present invention the activated oligomer may optionally comprise a bivalent linker between the oligomer and the activated disulfide moiety. In another embodiment, the activated disulfide moiety has the formula —S—S(O)$_2$-substituted or unsubstituted C$_1$-C$_{12}$ alkyl or —S—S—C(O)O-substituted or unsubstituted C$_1$-C$_{12}$ alkyl. Preferred activated disulfide moieties are methane thiosulfonate and dithiocarbomethoxy. In further embodiments, the activated disulfide is substituted or unsubstituted dithiopyridyl, substituted or unsubstituted dithiobenzothiazolyl, or substituted or unsubstituted dithiotetrazolyl. Preferred activated disulfides are 2-dithiopyridyl, 2-dithio-3-nitropyridyl, 2-dithio-5-nitropyridyl, 2-dithiobenzothiazolyl, N-(C$_1$-C$_{12}$ alkyl)-2-dithiopyridyl, 2-dithiopyridyl-N-oxide, or 2-dithio-1-methyl-1H-tetrazolyl.

Another aspect of the invention is a method of treating a subject with an activated oligomer, comprising the steps (a) providing an activated oligomer, said activated oligomer conjugated optionally with a bivalent linking group to an activated disulfide moiety; and (b) administering the activated oligomer to said subject.

Also disclosed are methods of treating a subject with an activated oligomer, the method comprising (a) providing an activated oligomer, said activated oligomer conjugated optionally with a bivalent linking group to an activated disulfide moiety; (b) obtaining a biological substance from the subject; (c) contacting the biological substance with said activated oligomer thereby producing an oligomer-linked biological substance; and (d) administering said oligomer-linked biological substance to said subject.

Also disclosed are methods of treating a subject with an activated oligomer, the method comprising (a) providing an activated oligomer, said activated oligomer conjugated optionally with a bivalent linking group to an activated disulfide moiety; (b) contacting a biological substance with said activated oligomer thereby producing an oligomer-linked biological substance; and (c) administering said oligomer-linked biological substance to said subject.

In one aspect of the present invention, the activated oligomer is an oligonucleotide, a peptide nucleic acid, or a morpholino nucleic acid. A more preferred activated oligomer is an oligonucleotide. In some embodiments, the oligonucleotide comprises at least one 2'-modified nucleotide, wherein the 2'-modification is selected from halogen, alkoxy, substituted alkoxy, amino, or substituted amino. Preferred 2'-modifications are fluoro, methoxy, methoxyethoxy, O-allyl, dimethylaminooxyethoxy and amino. In some embodiments, the oligonucleotide comprises at least one phosphodiester internucleoside linkage. In another embodiment, the oligonucleotide comprises at least one phosphorothioate linkage.

In some embodiments, the activated oligomer is a peptide nucleic acid. In a preferred embodiment, the activated oligomer is a peptide nucleic acid of the formula:

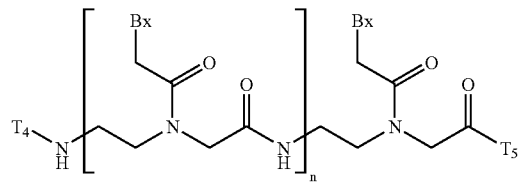

wherein, each Bx is independently a nucleobase;

T$_4$ is hydrogen, an amino protecting group, —C(O)R$_5$, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

T$_5$ is —OH, —N(Z$_1$)Z$_2$, R$_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-Z$_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)Z$_1$;

each J is O, S or NH—, $R_5$ is a carbonyl protecting group; and n is from 2 to about 50.

In some embodiments, the activated oligonucleotide is a double stranded oligonucleotide. In a preferred embodiment, the double stranded oligonucleotide comprises a first strand and a second strand. In another embodiment, at least one nucleotide of the first or the second strand of the double-stranded oligonucleotide is 2'-modified, wherein the 2'modification is selected from halogen, alkoxy, substituted alkoxy, amino or substituted amino. Preferred 2'-modifications are fluoro, methoxy, methoxyethoxy, O-allyl, dimethylaminooxyethoxy and amino. In some embodiments, at least one oliogonucleotide of the first or the second strand of the double-stranded oligonucleotide comprises at least one phosphodiester internucleoside linkage. In another embodiment, at least one oliogonucleotide of the first or the second strand of the double-stranded oligonucleotide comprises at least one phosphorothioate linkage.

In some embodiments, the activated disulfide moiety has the formula —S—S(O)$_n$—R$_1$, wherein n is 0, 1, or 2; and $R_1$ is selected from substituted or unsubstituted heterocyclic, substituted or unsubstituted aliphatic, or —C(O)O—R$_2$, wherein $R_2$ is substituted or unsubstituted aliphatic.

In another embodiment, the activated disulfide moiety has the formula —S—S(O)$_2$-substituted or unsubstituted $C_1$-$C_{12}$ alkyl or —S—S—C(O)O-substituted or unsubstituted $C_1$-$C_{12}$ alkyl. Preferred activated disulfide moieties are methane thiosulfonate and dithiocarbomethoxy. In further embodiments, the activated disulfide is substituted or unsubstituted dithiopyridyl, substituted or unsubstituted dithiobenzothiazolyl, or substituted or unsubstituted dithiotetrazolyl. Preferred activated disulfides are 2-dithiopyridyl, 2-dithio-3-nitropyridyl, 2-dithio-5-nitropyridyl, 2-dithiobenzothiazolyl, N-($C_1$-$C_{12}$ alkyl)-2-dithiopyridyl, 2-dithiopyridyl-N-oxide, or 2-dithio-1-methyl-1H-tetrazolyl.

In some embodiments, the bivalent linking group is a bivalent substituted or unsubstituted aliphatic group. In another embodiment, the bivalent linking group has the formula -Q$_1$-G-Q$_2$-, wherein $Q_1$ and $Q_2$ are independently absent or selected from substituted or unsubstituted $C_1$-$C_{12}$ alkylene, substituted or unsubstituted alkarylene or —(CH$_2$)$_m$—O—(CH$_2$)$_p$—, wherein each m and p are, independently, an integer from 1 to about 10;

G is —NH—C(O)—, —C(O)—NH—, —NH—C(O)—NH—, —NH—C(S)—NH—, —NH—O—, NH—C(O)—O—, or —O—CH$_2$—C(O)—NH—.

Preferred bivalent linking groups are:

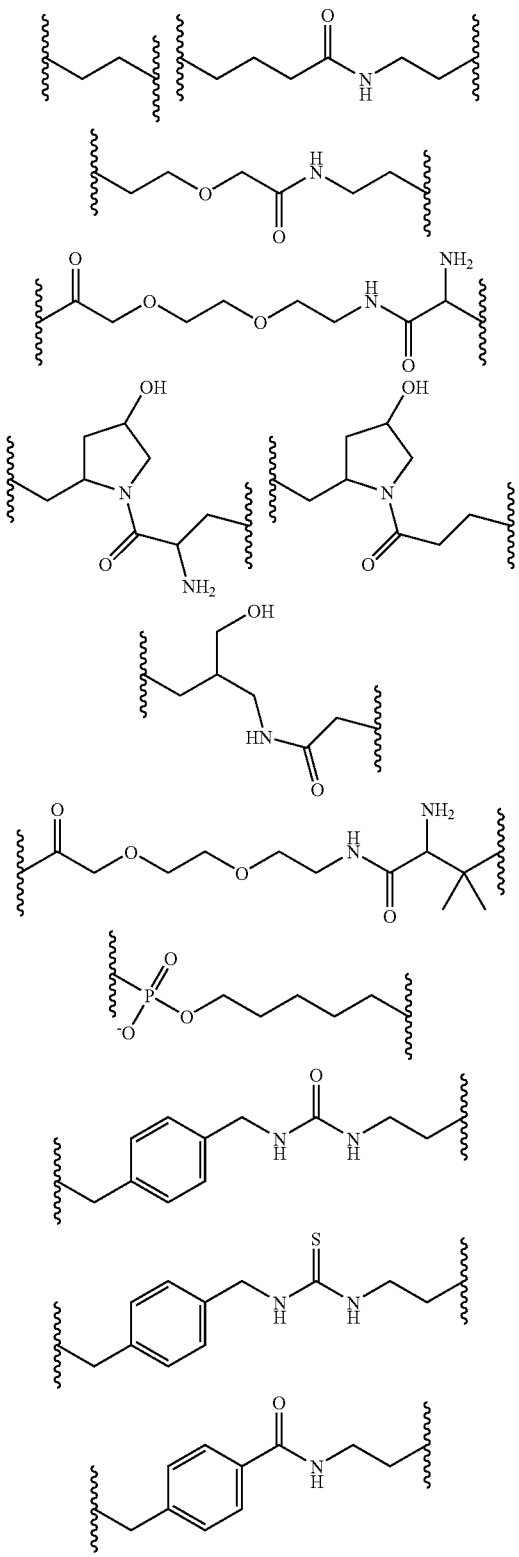

In certain embodiments of the methods of the present invention, the biological substance is a plasma protein, wherein said plasma protein is selected from serum albumin protein, transferring protein, ferritin protein, or immunoglobulin proteins. In preferred embodiments, the plasma proteins are purified plasma proteins or recombinant plasma proteins. In yet a more preferred embodiment, the plasma proteins are human plasma proteins. In preferred embodiments of the present invention, the serum albumin is purified human serum albumin or recombinant human serum albumin. In some embodiments the step of administering is intravenous, intraarterial, subcutaneous, intraperitoneal or intramuscular injection or infusion.

Another aspect of the present invention provides compounds, comprising a peptide nucleic acid (PNA), a bivalent linking group and an activated disulfide moiety. In some embodiments, the PNA comprises between 8 and 80 nucleobases. In other embodiments, the PNA comprises between 10 and 50 nucleobases. In further embodiments, the PNA comprises between 15 and 40 nucleobases. In a preferred embodiment, the PNA comprises between 15 and 25 nucleobases.

In some embodiments, the PNA is of the formula:

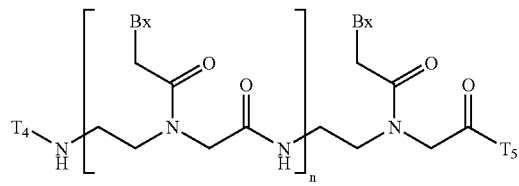

wherein
each Bx is independently a nucleobase;
$T_4$ is hydrogen, an amino protecting group, —C(O)$R_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;
$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;
$Z_1$ is hydrogen, $C_1$-$C_6$ alkyl, or an amino protecting group;
$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;
$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;
each J is O, S or NH—;
$R_5$ is a carbonyl protecting group; and
n is from 2 to about 50.

In some embodiments, the bivalent linking group of the oligomeric compound is a bivalent substituted or unsubstituted aliphatic group. In another embodiment, the bivalent linking group has the formula -$Q_1$-G-$Q_2$-, wherein $Q_1$ and $Q_2$ are independently absent or selected from substituted or unsubstituted $C_1$-$C_{12}$ alkylene, substituted or unsubstituted alkarylene or —(CH$_2$)$_m$—O—(CH$_2$)$_p$—, wherein
each m and p are, independently, an integer from 1 to about 10;
G is —NH—C(O)—, —C(O)—NH—, —NH—C(O)—NH—, —NH—C(S)—NH—, —NH—O—, NH—C(O)—O—, or —O—CH$_2$—C(O)—NH—.

Preferred bivalent linking groups are:

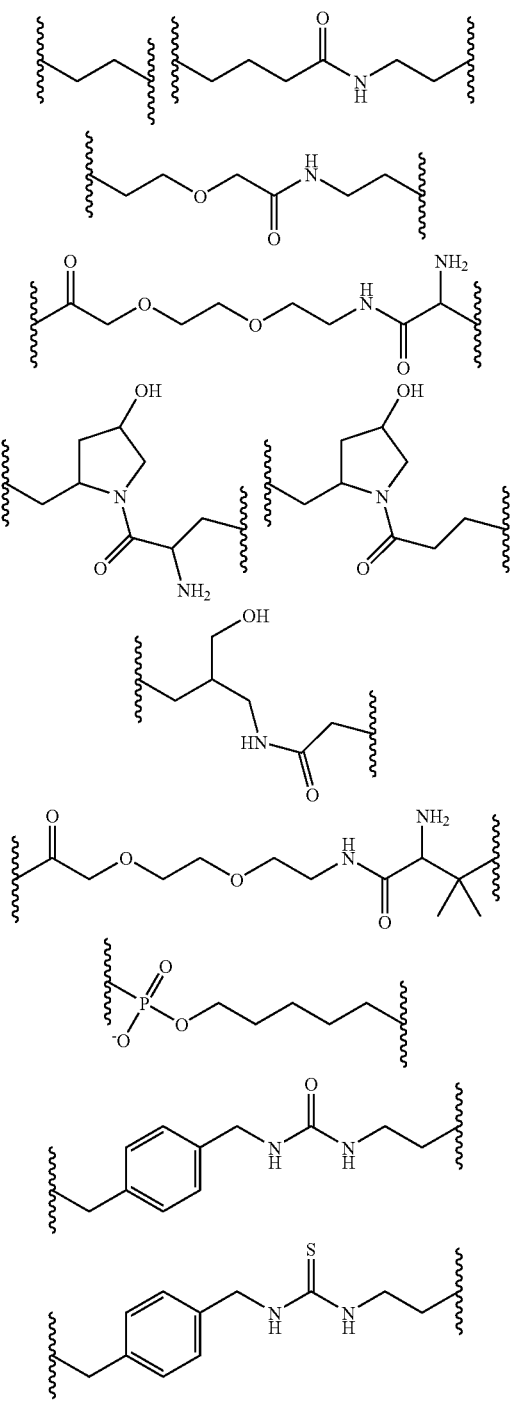

-continued

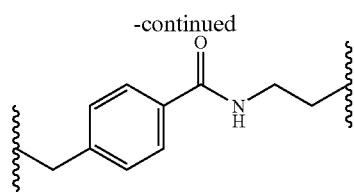

In some embodiments, the activated disulfide moiety of the oligomeric compound has the formula —S—S(O)$_n$—R$_1$, wherein n is 0, 1, or 2; and R$_1$ is selected from substituted or unsubstituted heterocyclic, substituted or unsubstituted aliphatic, or —C(O)O—R$_2$, wherein R$_2$ is substituted or unsubstituted aliphatic.

In further embodiments, the activated disulfide moiety has the formula —S—S(O)$_2$-substituted or unsubstituted C$_1$-C$_{12}$ alkyl or —S—S—C(O)O-substituted or unsubstituted C$_1$-C$_{12}$ alkyl. Preferred activated disulfide moieties are methane thiosulfonate and dithiocarbomethoxy. In further embodiments; the activated disulfide is substituted or unsubstituted dithiopyridyl, substituted or unsubstituted dithiobenzothiazolyl, or substituted or unsubstituted dithiotetrazolyl. Preferred activated disulfides are 2-dithiopyridyl, 2-dithio-3-nitropyridyl, 2-dithio-5-nitropyridyl, 2-dithiobenzothiazolyl, N-(C$_1$-C$_{12}$ alkyl)-2-dithiopyridyl, 2-dithiopyridyl-N-oxide, or 2-dithio-1-methyl-1H-tetrazolyl.

Another aspect of the present invention provides compounds, comprising a double-stranded oligonucleotide, comprising a first oligonucleotide and a second oligonucleotide, wherein at least one of said first or second oligonucleotides further comprises a bivalent linking group and an activated disulfide moiety.

In one embodiment, the composition comprises a double-stranded oligonucleotide, comprising a first oligonucleotide and a second oligonucleotide, which form a complementary pair of siRNA oligonucleotides. In another embodiment, the composition comprises a double stranded oligonucleotide, comprising a first oligonucleotide and a second oligonucleotide which form an antisense/sense pair of oligonucleotides.

In some embodiments, the first or second oligonucleotide of the double-stranded oligonucleotide comprises between 8 and 80 nucleobases. In other embodiments, the first or second oligonucleotide of the double-stranded oligonucleotide comprises between 10 and 50 nucleobases. In further embodiments, the first or second oligonucleotide of the double-stranded oligonucleotide comprises between 15 and 40 nucleobases. In a preferred embodiment, the first or second oligonucleotide of the double-stranded oligonucleotide comprises between 15 and 25 nucleobases.

In some embodiments, the bivalent linking group of the double stranded oligonucleotide is a bivalent substituted or unsubstituted aliphatic group. In another embodiment, the bivalent linking group has the formula -Q$_1$-G-Q$_2$-, wherein Q$_1$ and Q$_2$ are independently absent or selected from substituted or unsubstituted C$_1$-C$_{12}$ alkylene, substituted or unsubstituted alkarylene or —(CH$_2$)$_m$—O—(CH$_2$)$_p$—, wherein each m and p are, independently, an integer from 1 to about 10;

G is —NH—C(O)—, —C(O)—NH—, —NH—C(O)—NH—, —NH—C(S)—NH—, —NH—O—, NH—C(O)—O—, or —O—CH$_2$—C(O)—NH—.

Preferred bivalent linking group s are:

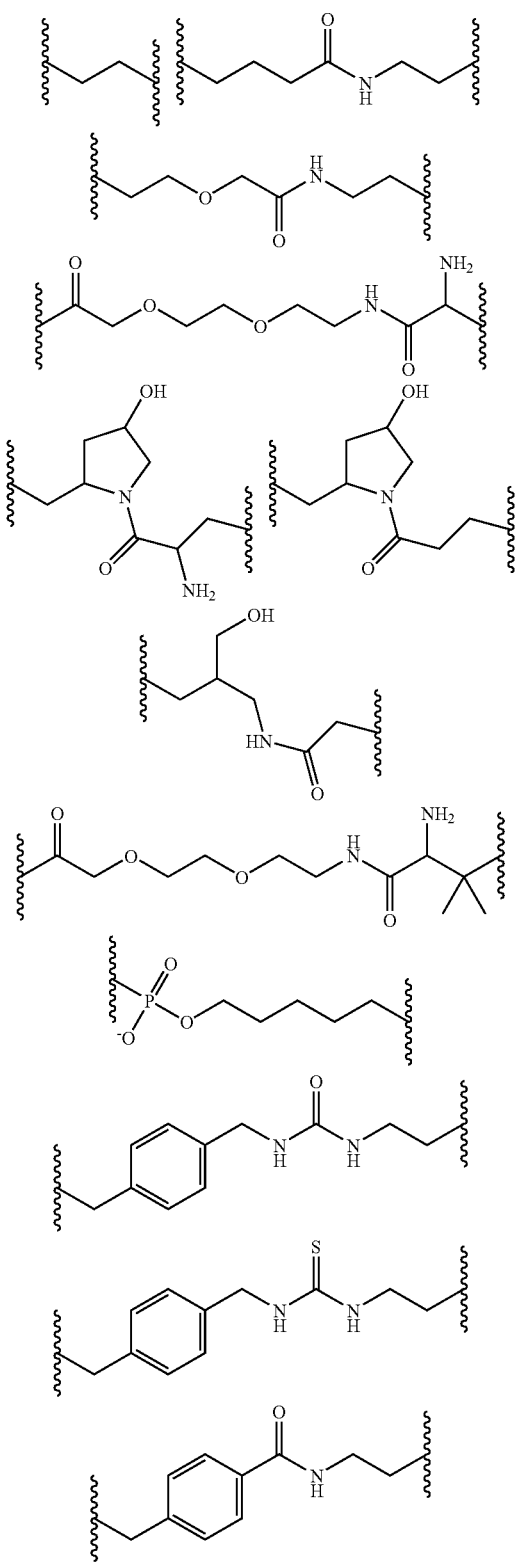

In some embodiments, the activated disulfide moiety of the double stranded oligonucleotide has the formula —S—S(O)$_n$—R$_1$, wherein n is 0, 1, or 2; and R$_1$ is selected from substituted or unsubstituted heterocyclic, substituted or unsubstituted aliphatic, or —C(O)O—R$_2$, wherein R$_2$ is substituted or unsubstituted aliphatic.

In another embodiment, the activated disulfide moiety has the formula —S—S(O)$_2$-substituted or unsubstituted C$_1$-C$_{12}$ alkyl or —S—S—C(O)O-substituted or unsubstituted C$_1$-C$_{12}$ alkyl. Preferred activated disulfide moieties are methane thiosulfonate and dithiocarbomethoxy. In further embodiments, the activated disulfide is substituted or unsubstituted dithiopyridyl, substituted or unsubstituted dithiobenzothiazolyl, or substituted or unsubstituted dithiotetrazolyl. Preferred activated disulfides are 2-dithiopyridyl, 2-dithio-3nitropyridyl, 2-dithio-5-nitropyridyl, 2-dithiobenzothiazolyl, N-(C$_1$-C$_{12}$ alkyl)-2-dithiopyridyl, 2-dithiopyridyl-N-oxide, or 2-dithio-1-methyl-1H-tetrazolyl.

Also within the scope of the present invention are processes of making any compound described herein via those methods delineated herein. It also should be understood that the embodiments specifically described herein are not limiting and it shall be apparent to one of ordinary skill in the art that additional embodiments not specifically mentioned are within the scope of the instant application.

BRIEF DESCRIPTION OF THE DRAWINGS

FIG. 3 depicts the effect of plasma protein binding on the enzymatic stability of PNA-peptide conjugates (a) without (ISIS309145) and (b) with (ISIS347349) activated disulfide groups.

FIG. 4 depicts tissue distribution in percent recovered dose of radiolabeled Isis 358346 in male Balb/c mice administered IV either free (a) or pre-bound (b) to plasma.

FIG. 5 depicts the plasma protein binding capacity for ISIS 386773 and ISIS 364615 as a function of their plasma concentration.

FIG. 6 depicts the release kinetics of ISIS 386773 from plasma proteins after the addition of GSH.

FIG. 7 depicts the binding kinetics of ISIS 386773 to plasma proteins.

DETAILED DESCRIPTION OF THE INVENTION

Definitions

Figure 1:
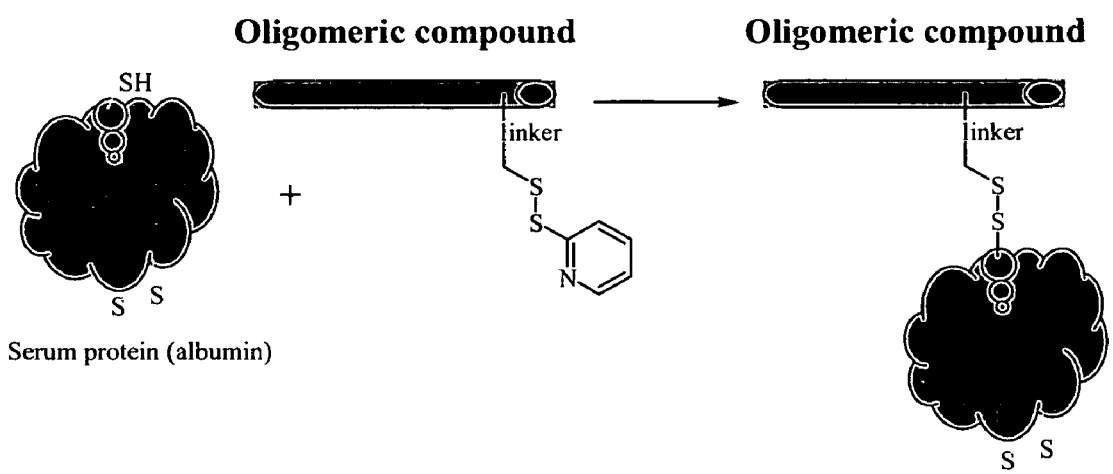
FIG. 1 is a schematic representation of the covalent attachment of oligomeric compounds containing activated disulfides to plasma proteins via biologically cleavable disulfide linker using a thiol-activated cysteine.

Listed below are definitions of various terms used to describe this invention. These definitions apply to the terms as they are used throughout this specification and claims, unless otherwise limited in specific instances, either individually or as part of a larger group. All terms appearing herein which are not specifically defined, shall be accorded the meaning that one of ordinary skill in the relevant art would attached to said term.

General Chemistry

The term "alkyl," as used herein, refers to saturated, straight chain or branched hydrocarbon moieties containing up to twenty four carbon atoms. The terms "C$_1$-C$_6$ alkyl" and "C$_1$-C$_{12}$ alkyl" as used herein, refer to saturated, straight chain or branched hydrocarbon moieties containing one to six carbon atoms and one to twelve carbon atoms respectively. Examples of alkyl groups include, but are not limited to, methyl, ethyl, propyl, isopropyl, n-hexyl, octyl, decyl, dodecyl and the like.

An "aliphatic group," as used herein, refers to an acyclic, non-aromatic moiety that may contain any combination of carbon atoms, hydrogen atoms, halogen atoms, oxygen, nitrogen, sulfur, phosphorus or other atoms, and optionally contain one or more units of unsaturation, e.g., double and/or triple bonds. An aliphatic group may be straight chained, or branched and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

Suitable substituents of the present invention include, but are not limited to, —F, —Cl, —Br, —I, —OH, protected hydroxy, aliphatic ethers, aromatic ethers, oxo, azido, imino, oximino, —NO$_2$, —CN, —COOH, —C$_1$-C$_{12}$-alkyl optionally substituted, C$_2$-C$_{12}$-alkenyl optionally substituted, —C$_2$-C$_{12}$-alkynyl optionally substituted, —NH$_2$, protected amino, —NH—C$_1$-C$_{12}$-alkyl, —NH—C$_2$-C$_{12}$-alkenyl, —NH—C$_2$-C$_{12}$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, —CONH-heterocycloalkyl, —CO$_2$—C$_1$-C$_{12}$-alkyl, —CO$_2$—C$_2$-C$_{12}$-alkenyl, —CO$_2$—C$_2$-C$_{12}$-alkynyl, —CO$_2$—C$_3$-C$_{12}$-cycloalkyl, —CO$_2$-aryl, —CO$_2$-heteroaryl, —CO$_2$-heterocycloalkyl, —OCO$_2$H, —OCO$_2$—C$_2$-C$_2$-alkyl, —OCO$_2$—C$_2$-C$_{12}$-alkenyl, —OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)—heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_2$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)$NH_2$, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_2$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_2$-alkyl, —$SO_2$NH—$C_2$-$C_{12}$-alkenyl, —$SO_2$NH—$C_2$-$C_{12}$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, aryl, arylalkyl, heteroaryl, heteroarylalkyl, heterocycloalkyl, —$C_3$-$C_{12}$-cycloalkyl, polyalkoxyalkyl, polyalkoxy, methoxymethoxy, methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls and the like can be further substituted.

The term "alkenyl" as used herein, refers to a straight chain or branched hydrocarbon moiety containing up to twenty four carbon atoms having at least one carbon-carbon double bond. The terms "$C_2$-$C_6$ alkenyl" and "$C_2$-$C_{12}$ alkenyl," as used herein refer to straight chain or branched hydrocarbon moieties containing two to six carbon atoms and two to twelve carbon atoms respectively and having at least one carbon-carbon double bond. Examples of alkenyl groups include, but are not limited to, ethenyl, propenyl, butenyl, 1-methyl-2-buten-1-yl, alkadienes and the like.

The term "substituted alkenyl," as used herein, refers to an "alkenyl" or "$C_2$-$C_{12}$ alkenyl" or "$C_2$-$C_6$ alkenyl" group as previously defined, substituted by one, two, three or more substituents.

The term "alkynyl" as used herein, refers to a straight chain or branched hydrocarbon moiety containing up to twenty four carbon atoms and having at least one carbon-carbon triple bond. The terms "$C_2$-$C_6$ alkynyl" and "$C_2$-$C_{12}$ alkynyl," as used herein, refer to straight chain or branched hydrocarbon moieties containing two to six carbon atoms and two to twelve carbon atoms respectively and having at least one carbon-carbon triple bond. Examples of alkynyl groups include, but are not limited to, ethynyl, 1-propynyl, 1-butynyl, and the like.

The term "substituted alkynyl," as used herein, refers to an "alkynyl" or "$C_2$-$C_6$ alkynyl" or "$C_2$-$C_{12}$ alkynyl" group as previously defined, substituted by one, two, three or more substituents.

The term "alkoxy," as used herein, refers to an aliphatic group, as previously defined, attached to the parent molecular moiety through an oxygen atom. Examples of alkoxy include, but are not limited to, methoxy, ethoxy, propoxy, isopropoxy, n-butoxy, sec-butoxy, tert-butoxy, n-pentoxy, neopentoxy, n-hexoxy and the like.

The term "substituted alkoxy," as used herein, refers to an alkoxy group as previously defined substituted with one, two, three or more substituents.

The terms "halo" and "halogen," as used herein, refer to an atom selected from fluorine, chlorine, bromine and iodine.

The terms "aryl" or "aromatic," as used herein, refer to a mono-, bi- or tri-cyclic carbocyclic ring system having one, two or three aromatic rings. Examples of aryl groups include, but not limited to, phenyl, naphthyl, tetrahydronaphthyl, indanyl, idenyl and the like.

The terms "substituted aryl" or "substituted aromatic," as used herein, refer to an aryl or aromatic group as previously defined substituted by one, two, three or more substituents.

The term "arylalkyl," as used herein, refers to an aryl group attached to the parent molecular moiety via a $C_1$-$C_3$ alkyl or $C_1$-$C_6$ alkyl residue. Examples include, but are not limited to, benzyl, phenethyl and the like.

The term "substituted arylalkyl," as used herein, refers to an arylalkyl group as previously defined, substituted by one, two, three or more substituents.

The terms "heteroaryl" or "heteroaromatic," as used herein, refer to a mono-, bi-, or tri-cyclic aromatic radical or ring having from five to ten ring atoms of which at least one ring atom is selected from S, O and N; zero, one, two or three ring atoms are additional heteroatoms independently selected from S, O and N; and the remaining ring atoms are carbon, wherein any N or S contained within the ring may be optionally oxidized. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the parent molecular moiety through a carbon or hetero atom.

The terms "substituted heteroaryl" or "substituted heteroaromatic," as used herein, refer to a heteroaryl or heteroaromatic group as previously defined, substituted by one, two, three, or more substituents.

The term "alicyclic," as used herein, denotes a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo [2.2.1]heptyl, bicyclo [2.2.2] octyl and the like.

The term "substituted alicyclic," as used herein, refers to an alicyclic group as previously defined, substituted by one, two, three or more substituents.

The terms "heterocyclic," or "heterocycloalkyl" as used herein, refer to a non-aromatic ring, comprising three or more ring atoms, or a bi- or tri-cyclic fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Examples of heterocyclic groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like.

The term "substituted heterocyclic," as used herein, refers to a heterocyclic group, as previously defined, substituted by one, two, three or more substituents.

The term "heteroarylalkyl," as used herein, refers to a heteroaryl group as previously defined, attached to the parent molecular moiety via an alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by one, two, three or more substituents.

The term "alkylamino" refers to a group having the structure —NH-alkyl.

The term "dialkylamino" refers to a group having the structure —N(alkyl)$_2$ and cyclic amines. Examples of dialkylamino include, but are not limited to, dimethylamino, diethylamino, methylethylamino, piperidino, morpholino and the like.

The term "alkoxycarbonyl" refers to an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH-alkyl or —C(O)N(alkyl)$_2$, —C(O)NH$_2$, —NHC(O)alkyl, —N(alkyl)C(O)(alkyl) and the like.

The term "protecting group," as used herein, refers to a labile chemical moiety which is known in the art to protect a hydroxyl, amino or thiol group against undesired reactions during synthetic procedures. After said synthetic procedure(s) the protecting group as described herein may be selectively removed. Protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include, but are not limited to, benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl (BOC), isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl (Alloc), acetyl (Ac), formyl, chloroacetyl, trifluoroacetyl, methoxyacetyl, phenoxyacetyl, benzoyl (Bz), methyl, t-butyl, 2,2,2-trichloroethyl, 2-trimethylsilyl ethyl, 1,1-dimethyl-2-propenyl, 3-methyl-3-butenyl, allyl, benzyl (Bn), para-methoxybenzyldiphenylmethyl, triphenylmethyl (trityl), 4,4'-dimethoxytriphenylmethyl (DMT), substituted or unsubstituted 9-(9-phenyl)xanthenyl (pixyl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are DMT and substituted or unsubstituted pixyl.

Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl (BOC), 9-fluorenylmethoxycarbonyl (Fmoc), benzyloxycarbonyl, and the like.

Thiol protecting groups as known in the art are described generally in T. H. Greene and P. G. M. Wuts, *Protective Groups in Organic Synthesis,* 3rd edition, John Wiley & Sons, New York (1999). Examples of thiol protecting groups include, but are not limited to, triphenylmethyl (Trt), benzyl (Bn), and the like.

The term "protected hydroxyl group," as used herein, refers to a hydroxyl group protected with a protecting group, as previously defined.

The term "protected amino group," as used herein, refers to an amino group protected with a protecting group, as previously defined.

The term "protected thiol group," as used herein, refers to a thiol group protected with a protecting group, as previously defined.

The term "acyl" includes residues derived from substituted or unsubstituted acids including, but not limited to, carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane, toluene and the like, halogenated hydrocarbons, such as methylene chloride, ethylene chloride, chloroform, and the like, heterocyclic compounds, such as tetrahydrofuran, N-methylpyrrolidinone and the like, and ethers such as diethyl ether, bis-methoxymethyl ether and the like. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: Organic Solvents Physical Properties and Methods of Purification, 4th ed., edited by John A. Riddick et al, Vol. II, in the Techniques of Chemistry Series, John Wiley & Sons, NY, 1986. Aprotic solvents useful in the processes of the present invention include, but are not limited to, toluene, acetonitrile, DMF, THF, dioxane, MTBE, diethylether, NMP, acetone, hydrocarbons, and haloaliphatics.

The term "protic solvent" or "protogenic solvent" as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protic solvents may be found in organic chemistry textbooks or in specialized monographs, for example: Organic Solvents Physical Properties and Methods of Purification, 4th ed., edited by John A. Riddick et al., Vol. II, in the Techniques of Chemistry Series, John Wiley & Sons, NY, 1986.

The synthesized compounds can be separated from a reaction mixture and further purified by a method such as column chromatography, high pressure liquid chromatography, or recrystallization. Further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Gene Modulation

The term "subject" as used herein refers to an animal. Preferably the animal is a mammal. More preferably the mammal is a human. A subject also refers to, for example, monkeys, dogs, cats, horses, cows, pigs, rabbits, rats, mice, guinea pigs, and the like.

As used herein, the term "target nucleic acid" or "nucleic acid target" is used for convenience to encompass any nucleic acid capable of being targeted including without limitation DNA, RNA (including pre-mRNA and mRNA or portions thereof) transcribed from such DNA, and also cDNA derived from such RNA. In one embodiment of the invention, the target nucleic acid is a messenger RNA. In another embodiment, the degradation of the targeted messenger RNA is facilitated by a RISC complex that is formed with oligomeric compounds of the invention. In another embodiment, the degradation of the targeted messenger RNA is facilitated by a nuclease such as RNaseH.

The hybridization of an oligomeric compound of this invention with its target nucleic acid is generally referred to as "antisense". Consequently, one mechanism in the practice of some embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently suitable to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the desired form of modulation of expression and mRNA is often a desired target nucleic acid.

The compounds and methods of the present invention are also useful in the study, characterization, validation and modulation of small non-coding RNAs. These include, but are not limited to, microRNAs (miRNA), small nuclear RNAs (snRNA), small nucleolar RNAs (snoRNA), small temporal RNAs (stRNA) and tiny non-coding RNAs (tncRNA) or their precursors or processed transcripts or their association with other cellular components.

Small non-coding RNAs have been shown to function in various developmental and regulatory pathways in a wide range of organisms, including plants, nematodes and mammals. MicroRNAs are small non-coding RNAs that are processed from larger precursors by enzymatic cleavage and inhibit translation of mRNAs. stRNAs, while processed from precursors much like miRNAs, have been shown to be involved in developmental timing regulation. Other non-coding small RNAs are involved in events as diverse as cellular splicing of transcripts, translation, transport, and chromosome organization.

As modulators of small non-coding RNA function, the compounds of the present invention find utility in the control and manipulation of cellular functions or processes such as regulation of splicing, chromosome packaging or methylation, control of developmental timing events, increase or decrease of target RNA expression levels depending on the timing of delivery into the specific biological pathway and translational or transcriptional control. In addition, the compounds of the present invention can be modified in order to optimize their effects in certain cellular compartments, such as the cytoplasm, nucleus, nucleolus or mitochondria.

The compounds of the present invention can further be used to identify components of regulatory pathways of RNA processing or metabolism as well as in screening assays or devices.

Oligomeric Compounds

In the context of the present invention, the term "oligomeric compound" refers to a polymeric structure capable of hybridizing a region of a nucleic acid molecule. This term includes oligonucleotides, oligonucleosides, oligonucleotide analogs, oligonucleotide mimetics and combinations of these. Oligomeric compounds are routinely prepared linearly but can be joined or otherwise prepared to be circular and may also include branching. Oligomeric compounds can include double stranded constructs such as for example two strands hybridized to form double stranded compounds. The double stranded compounds can be linked or separate and can include overhangs on the ends. In general, an oligomeric compound comprises a backbone of linked momeric subunits where each linked momeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified giving rise to a plurality of motifs for the resulting oligomeric compounds including hemimers, gapmers and chimeras.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions which function in a similar manner to oligonulceotides. Such non-naturally occurring oligonucleotides are often desired over the naturally occurring forms because of desirable properties such as, for example, enhanced cellular uptake, enhanced affinity for nucleic acid target and increased stability in the presence of nucleases.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Further included in the present invention are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of antisense oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In addition to the modifications described above, the nucleosides of the oligomeric compounds of the invention can have a variety of other modification so long as these other modifications either alone or in combination with other nucleosides enhance one or more of the desired properties described above. Thus, for nucleotides that are incorporated into oligonucleotides of the invention, these nucleotides can have sugar portions that correspond to naturally-occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar. Additional nucleosides amenable to the present invention having altered base moieties and or altered sugar moieties are disclosed in U.S. Pat. No. 3,687,808 and PCT application PCT/US89/02323.

The term "nucleobase," as used herein, is intended to by synonymous with "nucleic acid base or mimetic thereof." In general, a nucleobase is any substructure that contains one or more atoms or groups of atoms capable of hydrogen bonding to a base of an oligonucleotide.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C{\equiv}C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H- pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified Nucleobases

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

The term "universal base" as used herein, refers to a moiety that may be substituted for any base. The universal base need not contribute to hybridization, but should not significantly detract from hybridization and typically refers to a monomer in a first sequence that can pair with a naturally occurring base, i.e A, C, G, T or U at a corresponding position in a second sequence of a duplex in which one or more of the following is true: (1) there is essentially no pairing between the two; or (2) the pairing between them occurs non-discriminately with each of the naturally occurring bases and without significant destabilization of the duplex. Exemplary universal bases include, without limitation, inosine, 5-nitroindole and 4-nitrobenzimidazole.

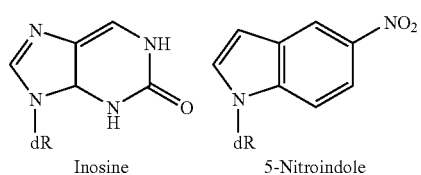
Inosine     5-Nitroindole

-continued

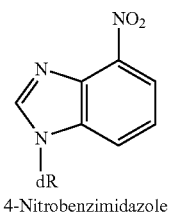
4-Nitrobenzimidazole

Additional examples of universal bases include, but are not limited to, those shown below. For further examples and descriptions of universal bases see Survey and summary: the applications of universal DNA base analogs. Loakes, D. *Nucleic Acids Research*, 2001, 29, 12, 2437-2447.

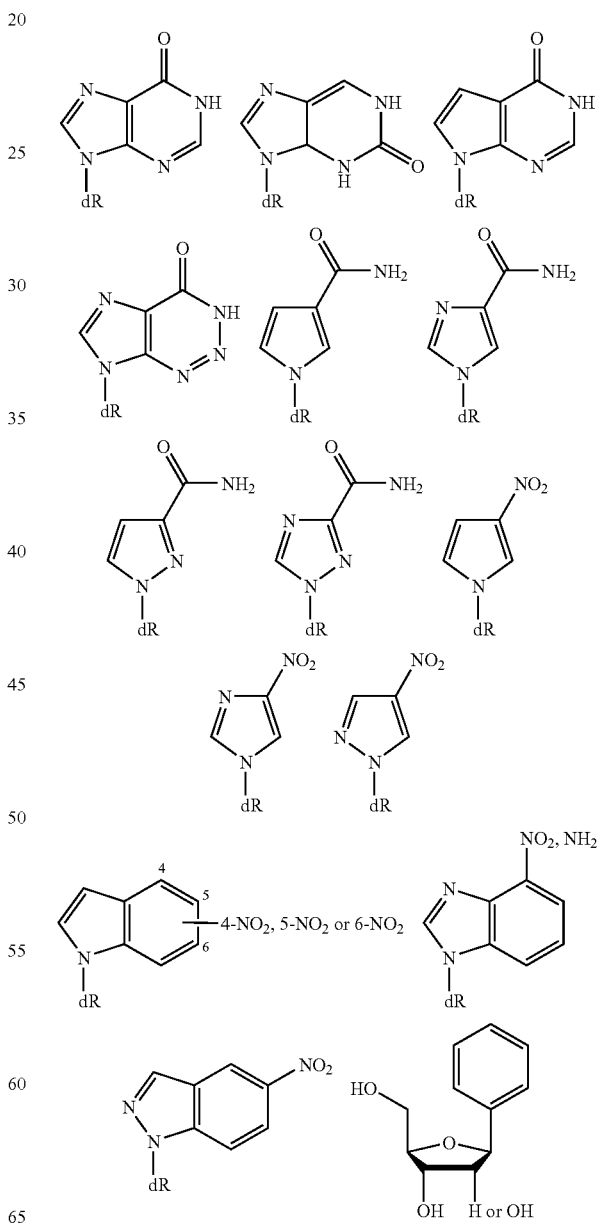

-continued

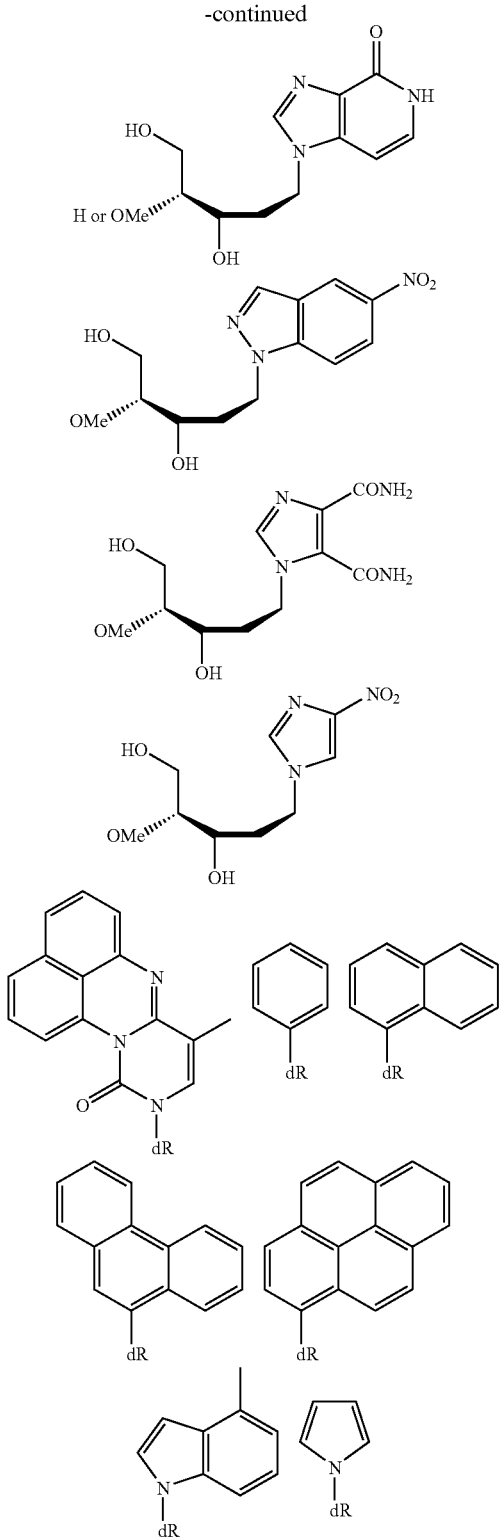

The term "hydrophobic base" as used herein, refers to a monomer in a first sequence that can pair with a naturally occurring base, i.e A, C, G, T or U at a corresponding position in a second sequence of a duplex in which one or more of the following is true: (1) the hydrophobic base acts as a non-polar close size and shape mimic (isostere) of one of the naturally occurring nucleosides; or (2) the hydrophobic base lacks all hydrogen bonding functionality on the Watson-Crick pairing edge.

Examples of adenine isosteres include, but are not limited to those shown below. For further examples and definitions of adenine isosteres see Probing the requirements for recognition and catalysis in Fpg and MutY with nonpolar adenine isosteres. Francis, A W, Helquist, S A, Kool, E T, David, S S. *J. Am. Chem. Soc.*, 2003, 125, 16235-16242 or Structure and base pairing properties of a replicable nonpolar isostere for deoxyadenosine. Guckian, K M, Morales, J C, Kool, E T. *J. Org. Chem.*, 1998, 63, 9652-96565.

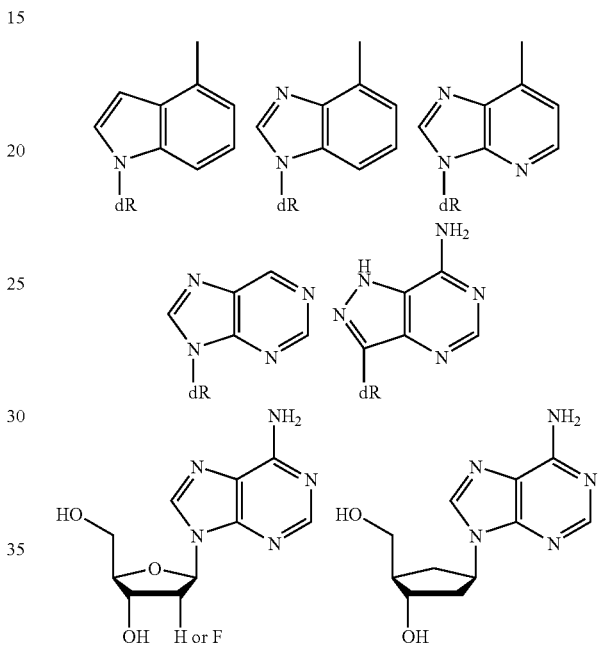

A non-limiting example of a cytosine isostere is 2-fluoro-4-methylbenzene deoxyribonucleoside, shown below. For additional information on cytosine isosteres see Hydrolysis of RNA/DNA hybrids containing nonpolar pyrimidine isosteres defines regions essential for HIV type polypurine tract selection. Rausch, J W, Qu, J, Yi-Brunozzi H Y, Kool, E T, LeGrice, S F J. *Proc. Natl. Acad. Sci.*, 2003, 100, 11279-11284.

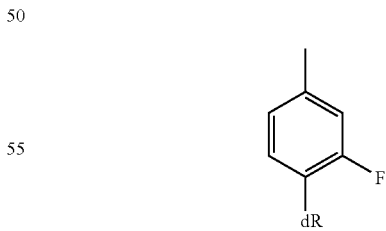

A non-limiting example of a guanosine isostere is 4-fluoro-6-methylbenzimidazole deoxyribonucleoside, shown below. For additional information on guanosine isosteres, see A highly effective nonpolar isostere of doeoxguanosine: synthesis, structure, stacking and base pairing. O'Neil, B M, Ratto, J E, Good, K L, Tahmassebi, D C, Helquist, S A, Morales, J C, Kool, E T. *J. Org. Chem.*, 2002, 67, 5869-5875.

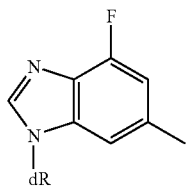

A non-limiting example of a thymidine isostere is 2,4-difluoro-5-toluene deoxyribonucleoside, shown below. For additional information on thymidine isosteres see A thymidine triphosphate shape analog lacking Watson-Crick pairing ability is replicated with high sequence selectivity. Moran, S, Ren, RX-F, Kool, E T. *Proc. Natl. Acad. Sci.,* 1997, 94, 10506-10511 or Difluorotoluene, a nonpolar isostere for thymidine, codes specifically and efficiently for adenine in DNA replication. *J. Am. Chem. Soc.* 1997, 119, 2056-2057.

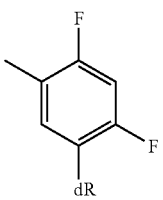

The term "promiscuous base" as used herein, refers to a monomer in a first sequence that can pair with a naturally occurring base, i.e A, C, G, T or U at a corresponding position in a second sequence of a duplex in which the promiscuous base can pair non-discriminately with more than one of the naturally occurring bases, i.e. A, C, G, T, U. Non-limiting examples of promiscuous bases are 6H,8H-3,4-dihydropyrimido[4,5-c][1,2]oxazin-7-one and $N^6$-methoxy-2,6-diaminopurine, shown below. For further information, see Polymerase recognition of synthetic oligodeoxyribonucleotides incorporating degenerate pyrimidine and purine bases. Hill, F.; Loakes, D.; Brown, D. M. *Proc. Natl. Acad. Sci.,* 1998, 95, 4258-4263.

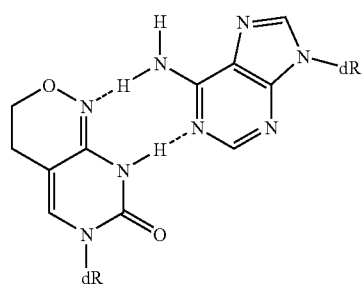

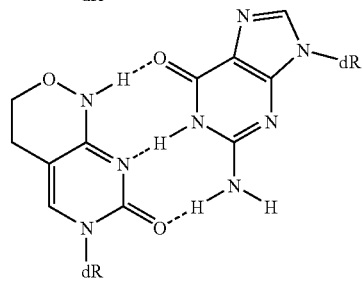

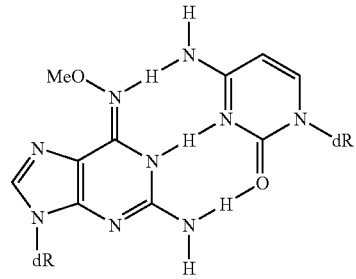

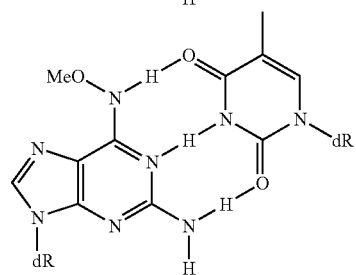

The term "size expanded base" as used herein, refers to analogs of naturally occurring nucleobases that are larger in size and retain their Watson-Crick pairing ability. Tow non-limiting examples of size-expanded bases are shown below. For further discussions of size expanded bases see A four-base paired genetic helix with expanded size. Liu, B, Gao, J, Lynch, S R, Saito, D, Maynard, L, Kool, E T., *Science,* 2003, 302, 868-871 and Toward a new genetic system with expanded dimension: size expanded analogues of deoxyadenosine and thymidine. Liu, H, Goa, J, Maynard, Y, Saito, D, Kool, E T, *J. Am. Chem. Soc.* 2004, 126, 1102-1109 and Expanded-Size Bases in Naturally Sized DNA: Evaluation of Steric Effects in Watson-Crick Pairing. Gao, J, Liu, H, Kool, E, *J. Am. Chem. Soc.* 2004, 126, 11826-11831.

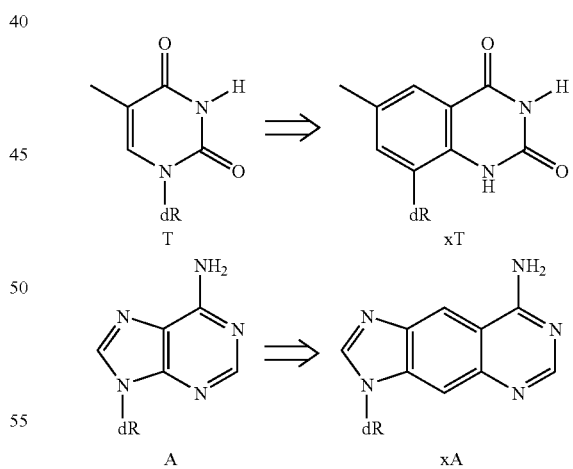

The term "fluorinated nucleobase" as used herein, refers to a nucleobase or nucleobase analog, wherein one or more of the aromatic ring substituents is a fluoroine atom. It may be possible that all of the ring substituents are fluoroine atoms. Some non-limiting examples of fluorinated nucleobase are shown below. For further examples of fluorinated nucleobases see fluorinated DNA bases as probes of electrostatic effects in DNA base stacking. Lai, J S, Q U, J, Kool, E T, *Angew. Chem. Int. Ed.,* 2003, 42, 5973-5977 and Selective pairing of polyfluorinated DNA bases, Lai, J S, Kool, E T, *J. Am. Chem. Soc.*, 2004, 126, 3040-3041 and The effect of universal fluorinated nucleobases on the catalytic activity of ribozymes, Kloppfer, A E, Engels, J W, *Nucleosides, Nucleotides & Nucleic Acids*, 2003, 22, 1347-1350 and Synthesis of 2'aminoalkyl-substituted fluorinated nucleobases and their influence on the kinetic properties of hammerhead ribozymes, Klopffer, A E, Engels, J W, *Chem Bio Chem.*, 2003, 5, 707-716.

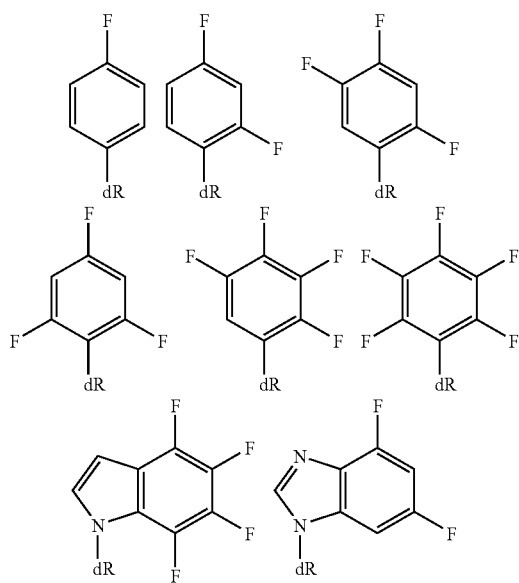

In some embodiments of the invention, oligomeric compounds, e.g. oligonucleotides, are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

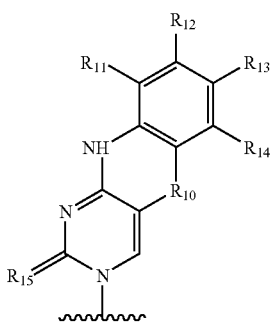

Representative cytosine analogs that make 3 hydrogen bonds with a guanosine in a second oligonucleotide include 1,3-diazaphenoxazine-2-one ($R_{10}$=O, $R_{11}$-$R_{14}$=H) [Kurchavov, et al., *Nucleosides and Nucleotides*, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$= —O—(CH$_2$)$_2$—NH$_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety. Such compounds include those having the formula:

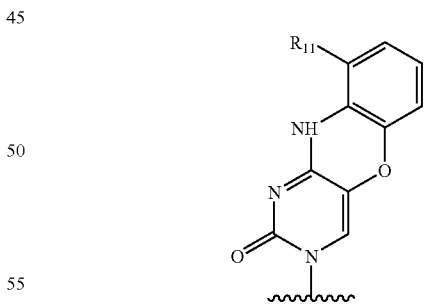

Wherein $R_{11}$ includes (CH$_3$)$_2$N—(CH$_2$)$_2$—O—; H$_2$N—(CH$_2$)$_3$—; Ph-CH$_2$—O—C(=O)—N(H)—(CH$_2$)$_3$—; H$_2$N—; Fluorenyl-CH$_2$—O—C(=O)—N(H)—(CH$_2$)$_3$—; Phthalimidyl-CH$_2$—O—C(=O)—N(H)—(CH$_2$)$_3$—; Ph-CH$_2$—O—C(=O)—N(H)—(CH$_2$)$_2$—O—; Ph-CH$_2$—O—C(=O)—N(H)—(CH$_2$)$_3$—O—; (CH$_3$)$_2$N—N(H)—(CH$_2$)$_2$—O—; Fluorenyl-CH$_2$—O—C(=O)—N(H)—(CH$_2$)$_2$—O—; Fluorenyl-CH$_2$—O—C(=O)—N(H)—(CH$_2$)$_3$—O—; H$_2$N—(CH$_2$)$_2$—O—CH$_2$—; N$_3$—(CH$_2$)$_2$—O—CH$_2$—; H$_2$N—(CH$_2$)$_2$—O—, and NH$_2$C(=NH)NH—.

Also disclosed are tricyclic heterocyclic compounds of the formula:

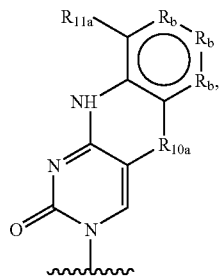

wherein:

$R_{10a}$ is O, S or N—CH$_3$; $R_{11a}$ is $A(Z)_{x1}$, wherein A is a spacer and Z independently is a label bonding group optionally bonded to a detectable label, but $R_{11a}$ is not amine, protected amine, nitro or cyano; and $R_b$ is independently —CH=, —N=, —C(C$_{1-8}$ alkyl)= or —C(halogen)=, but no adjacent $R_b$ are both —N=, or two adjacent $R_b$ are taken together to form a ring having the structure:

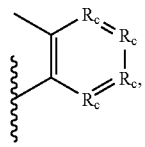

where $R_c$ is independently —CH=, —N=, —C(C$_{1-8}$ alkyl)= or —C(halogen)=, but no adjacent $R_b$ are both —N=.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K.-Y.; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further tricyclic and tetracyclic heteroaryl compounds amenable to the present invention include those having the formulas:

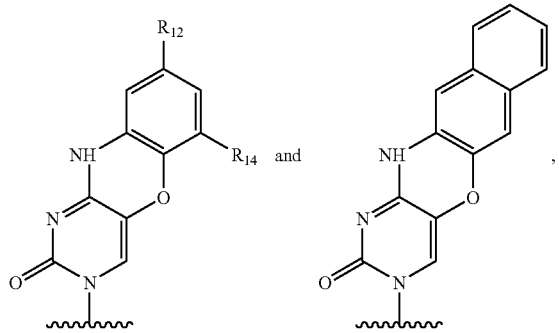

wherein $R_{14}$ is NO$_2$ or both $R_{14}$ and $R_{12}$ are independently —CH$_3$. The synthesis of these compounds is disclosed in U.S. Pat. No. 5,434,257, which issued on Jul. 18, 1995, U.S. Pat. No. 5,502,177, which issued on Mar. 26, 1996, and U.S. Pat. No. 5,646,269, which issued on Jul. 8, 1997, the contents of which are commonly assigned with this application and are incorporated herein in their entirety (hereinafter referred to as the "'257, '177 and '269 patents").

Further tricyclic heterocyclic compounds amenable to the present invention also disclosed in the '257, '177 and '269 patents include those having the formula:

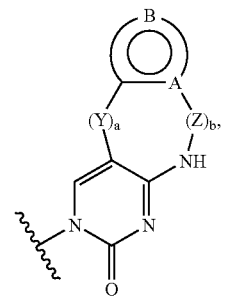

wherein a and b are independently 0 or 1 with the total of a and b being 0 or 1; A is N, C or CH; Y is S, O, C=O, NH or NCH$_2$, R$^6$; Z is C=O; B is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a C atom, 2 N ring heteroatoms separated by a carbon atom, or 3 N ring heteroatoms at least 2 of which are separated by a carbon atom, and wherein the aryl or heteroaryl ring carbon atoms are unsubstituted with other than H or at least 1 nonbridging ring carbon atom is substituted with R$^{20}$ or =O; or Z is taken together with A to form an aryl ring structure comprising 6 ring atoms wherein the aryl ring carbon atoms are unsubstituted with other than H or at least 1 nonbridging ring carbon atom is substituted with R$^6$ or =O; R$^6$ is independently H, C$_{1-6}$ alkyl, C$_{2-6}$ alkenyl, C$_{2-6}$ alkynyl, NO$_2$, N(R$^3$)$_2$, CN or halo, or an R$^6$ is taken together with an adjacent B group R$^6$ to complete a phenyl ring; R$^{20}$ is, independently, H, C$_{1-6}$ alkyl, C$_{2-6}$ alkyl, C$_{2-6}$ alkenyl, C$_{2-6}$ alkynyl, NO$_2$, N(R$^{21}$)$_2$, CN, or halo, or an R$^{20}$ is taken together with an adjacent R$^{20}$ to complete a ring containing 5 or 6 ring atoms, and tautomers, solvates and salts thereof; R$^{21}$ is, independently, H or a protecting group; R$^3$ is a protecting group or H; and tautomers, solvates and salts thereof.

More specific examples of bases included in the "257, 177 and 269" Patents are compounds of the formula:

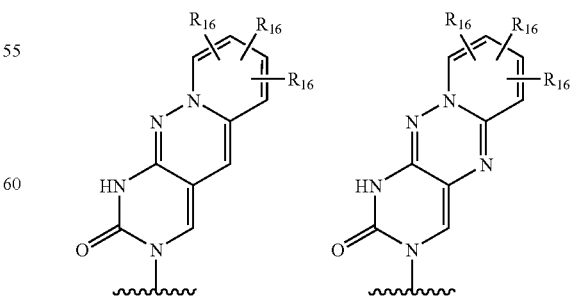

-continued

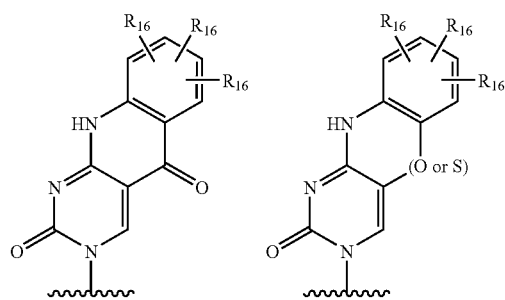
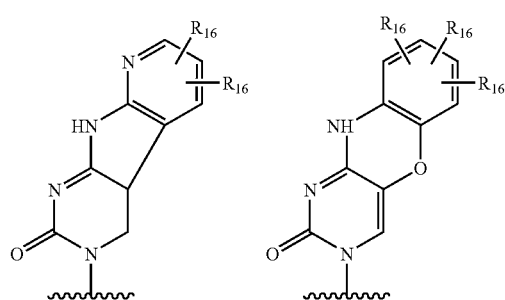
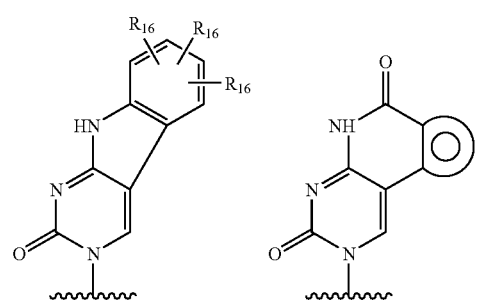
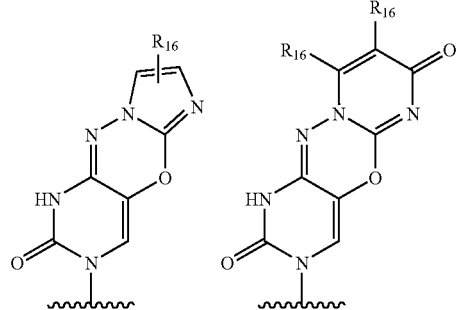
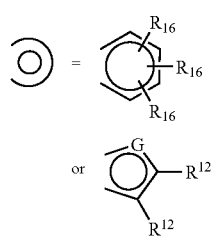

wherein each $R_{16}$, is, independently, selected from hydrogen and various substituent groups. Further polycyclic base moieties having the formula:

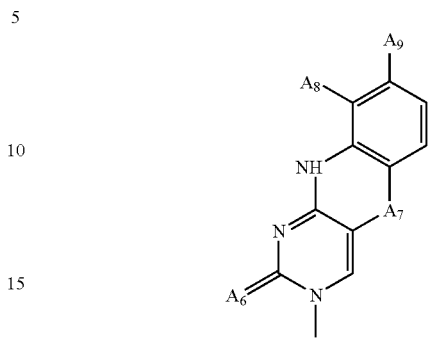

wherein: $A_6$ is O or S; $A_7$ is $CH_2$, N—$CH_3$, O or S; each $A_8$ and $A_9$ is hydrogen or one of $A_8$ and $A_9$ is hydrogen and the other of $A_8$ and $A_9$ is selected from the group consisting of:

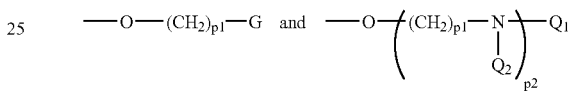

wherein: G is —CN, —$OA_{10}$, —$SA_{10}$, —N(H)$A_{10}$, —ON(H)$A_{10}$ or —C(=NH)N(H)$A_{10}$; $Q_1$ is H, —$NHA_{10}$, —C(=O)N(H)$A_{10}$, —C(=S)N(H)$A_{10}$ or —C(=NH)N(H)$A_{10}$; each $Q_2$ is, independently, H or Pg; $A_{10}$ is H, Pg, substituted or unsubstituted $C_1$-$C_{10}$ alkyl, acetyl, benzyl, —$(CH_2)_{p3}NH_2$, —$(CH_2)_{p3}$N(H)Pg, a D or L α-amino acid, or a peptide derived from D, L or racemic α-amino acids; Pg is a nitrogen, oxygen or thiol protecting group; each p1 is, independently, from 2 to about 6; p2 is from 1 to about 3; and p3 is from 1 to about 4; are disclosed in U.S. patent application Ser. No. 09/996,292 filed Nov. 28, 2001, which is commonly owned with the instant application, and is herein incorporated by reference.

Some particularly useful oligomeric compounds of the invention contain at least one nucleoside having one, two, three, or more aliphatic substituents, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—$CH_2CH_2OCH_3$, also known as 2'-O-(2-methoxyethyl) or 2'-MOE] (Martin et al., Helv. Chim. Acta, 1995, 78, 486), i.e., an alkoxyalkoxy group. A further preferred modification is 2'-dimethylaminooxyethoxy, i.e., a $O(CH_2)_2$ $ON(CH_3)_2$ group, also known as 2'-DMAOE. Representative aminooxy substituent groups are described in co-owned U.S. patent application Ser. No. 09/344,260, filed Jun. 25, 1999, entitled "Aminooxy-Functionalized Oligomers"; and U.S. patent application Ser. No. 09/370,541, filed Aug. 9, 1999, entitled "Aminooxy-Functionalized Oligomers and Methods for Making Same;" hereby incorporated by reference in their entirety.

Other particularly advantageous 2'-modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on nucleosides and oligomers, particularly the 3' position of the sugar on the 3' terminal nucleoside or at a 3'-position of a nucleoside that has a linkage from the 2'-position such as a 2'-5' linked oligomer and at the 5' position of a 5' terminal nucleoside. Oligomers may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

Representative guanidino substituent groups that are shown in formula are disclosed in co-owned U.S. patent application Ser. No. 09/349,040, entitled "Functionalized Oligomers", filed Jul. 7, 1999, issue fee paid on Oct. 23, 2002.

Representative acetamido substituent groups are disclosed in U.S. Pat. No. 6,147,200 which is hereby incorporated by reference in its entirety. Representative dimethylaminoethyloxyethyl substituent groups are disclosed in International Patent Application PCT/US99/17895, entitled "2'-O-Dimethylaminoethyloxyethyl-Modified Oligonucleotides", filed Aug. 6, 1999, hereby incorporated by reference in its entirety. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond, however, open linear structures are generally preferred. Within the oligonucleotide structure, the phosphate groups are commonly referred to as forming the internucleoside linkages of the oligonucleotide. The normal internucleoside linkage of RNA and DNA is a 3' to 5' phosphodiester linkage.

The oligomeric compounds in accordance with this invention can comprise from about 8 to about 80 nucleobases (i.e., from about 8 to about 80 linked nucleosides). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length, or any range therewithin.

In another embodiment, the oligomeric compounds of the invention are 12 to 50 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length, or any range therewithin.

In another embodiment, the oligomeric compounds of the invention are 15 to 30 nucleobases in length. One having ordinary skill in the art will appreciate that this embodies oligomeric compounds of 15, 16, 17, 18, 19, 20, 21, 22, 23, 24, 25, 26, 27, 28, 29, or 30 nucleobases in length, or any range therewithin.

Suitable oligomeric compounds are oligonucleotides from about 12 to about 50 nucleobases or from about 15 to about 30 nucleobases.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally desired. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Chimeric Oligomeric Compounds

It is not necessary for all positions in an oligomeric compound to be uniformly modified, and in fact more than one of the aforementioned modifications may be incorporated in a single oligomeric compound or even at a single monomeric subunit such as a nucleoside within an oligomeric compound. The present invention also includes oligomeric compounds which are chimeric oligomeric compounds. "Chimeric" oligomeric compounds or "chimeras," in the context of this invention, are oligomeric compounds which contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Such oligomeric compounds have also been referred to in the art as hybrids hemimers, gapmers or inverted gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Oligomer Mimetics

Another group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

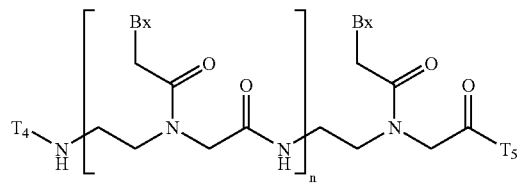

wherein
each Bx is independently a nucleobase;
$T_4$ is hydrogen, an amino protecting group, —C(O)$R_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;
$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;
$Z_1$ is hydrogen, $C_1$-$C_6$ alkyl, or an amino protecting group;
$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;
$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;
each J is O, S or NH;
$R_5$ is a carbonyl protecting group; and
n is from 2 to about 50.

Another modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be prefereably a methylene, ethylene (referred to in the art as ENA), or (—CH$_2$—)$_n$ group bridging the 2' oxygen atom and the 4' carbon atom wherein n is 1 to 10 (Singh et al., Chem. Commun., 1998, 4, 455-456). LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

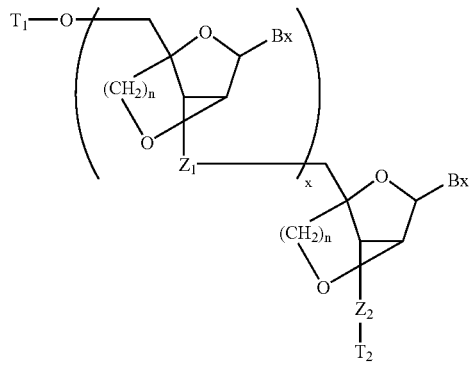

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U.S.A., 2000, 97, 5633-5638). The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNAs have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

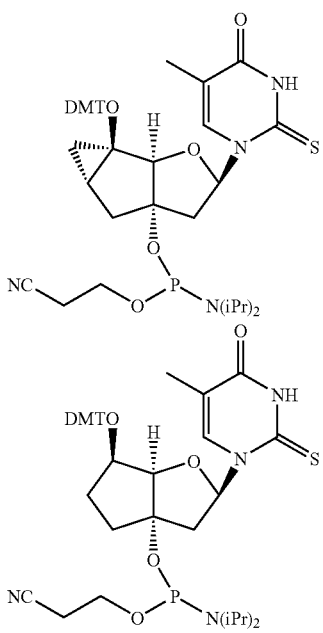

(see Steffens et al., Helv. Chim. Acta, 1997, 80, 2426-2439; Steffens et al., J. Am. Chem. Soc., 1999, 121, 3249-3255; and Renneberg et al., J. Am. Chem. Soc., 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

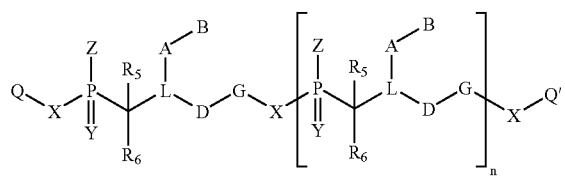

Another oligonucleotide mimetic has been reported wherein the furanosyl ring has been replaced by a cyclobutyl moiety.

Modified Internucleoside Linkages

Specific examples of antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain oligomeric compounds of the invention can also have one or more modified internucleoside linkages. One phosphorus containing modified internucleoside linkage is the phosphorothioate internucleoside linkage.

Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,196; 5,188,897; 5,264,423; 5,276,019;

5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In some embodiments of the invention, oligomeric compounds have one or more phosphorothioate and/or heteroatom internucleoside linkages, in particular —$CH_2$—NH—O—$CH_2$—, —$CH_2$—$N(CH_3)$—O—$CH_2$— (known as a methylene (methylimino) or MMI backbone), —$CH_2$—O—$N(CH_3)$—$CH_2$—, —$CH_2$—$N(CH_3)$—$N(CH_3)$—$CH_2$— and —O—$N(CH_3)$—$CH_2$—$CH_2$— (wherein the native phosphodiester internucleotide linkage is represented as —O—P(=O)(OH)—O—$CH_2$—). The MMI type internucleoside linkages are disclosed in the above referenced U.S. Pat. No. 5,489,677. Suitable amide internucleoside linkages are disclosed in the above referenced U.S. Pat. No. 5,602,240.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugars

Oligomeric compounds of the invention may also contain one or more substituted sugar moieties. Suitable oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. Another modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxyethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-Sugar substituent groups may be in the arabino (up) position or ribo (down) position. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety. Further representative sugar substituent groups include groups of formula Ia or Ib:

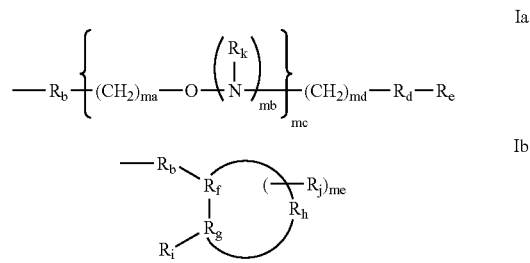

Ia

Ib wherein:

$R_b$ is O, S or NH;

$R_d$ is a single bond, O, S or C(=O);

$R_e$ is $C_1$-$C_{10}$ alkyl, $N(R_k)(R_m)$, $N(R_k)(R_n)$, N=C($R_p$)($R_q$), N=C($R_p$)($R_r$) or has formula Ic;

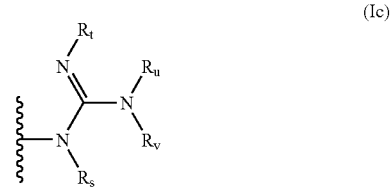

(Ic)

$R_p$ and $R_q$ are each independently hydrogen or $C_1$-$C_{10}$ alkyl;

$R_r$ is —$R_x$—$R_y$;

each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_k$ is hydrogen, an amino protecting group or —$R_x$—$R_y$;

$R_p$ is hydrogen, an amino protecting group or —$R_x$—$R_y$;

$R_x$ is a bond or a linking moiety;

$R_y$ is a chemical functional group, a conjugate group or a solid support medium;

each $R_m$ and $R_n$ is, independently, H, an amino protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)(R_v)$, guanidino and acyl where said acyl is an acid amide or an ester;

or $R_m$ and $R_n$, together, are an amino protecting group, are joined in a ring structure that optionally includes an additional heteroatom selected from N and O or are a chemical functional group;

$R_t$ is $OR_z$, $SR_z$, or $N(R_z)_2$;

each $R_z$ is, independently, H, $C_1$-$C_8$ alkyl, $C_1$-$C_8$ haloalkyl, $C(=NH)N(H)R_u$, $C(=O)N(H)R_u$ or $OC(=O)N(H)R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)$ $OR_k$, halo, $SR_k$ or CN;

$m_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

Representative substituents groups of Formula Ia are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula Ib are disclosed in U.S. patent application Ser. No. 09/123,108, filed Jul. 27, 1998, entitled "RNA Targeted 2'-Oligomeric compounds that are Conformationally Preorganized," hereby incorporated by reference in its entirety.

Sugar substituent groups also include $O[(CH_2)_nO]_mCH_3$, $O(CH_2)_nOCH_3$, $O(CH_2)_nNH_2$, $O(CH_2)_nCH_3$, $O(CH_2)_n$ $ONH_2$, and $O(CH_2)_nON[(CH_2)_nH]_2$, where n and m are from 1 to about 10.

Representative guanidino substituent groups that are shown in formula Ic are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethylaminoethyloxyethyl-Oligomeric compounds", filed Aug. 6, 1999, hereby incorporated by reference in its entirety.

Conjugates

Another substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, poly-ethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

3'-Endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the C. elegans system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

Scheme 1

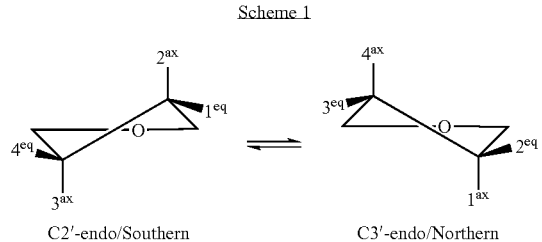

C2'-endo/Southern        C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in Scheme 1a, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.) Representative examples of modified nucleosides amenable to the present invention include, but are not limited to those shown below:

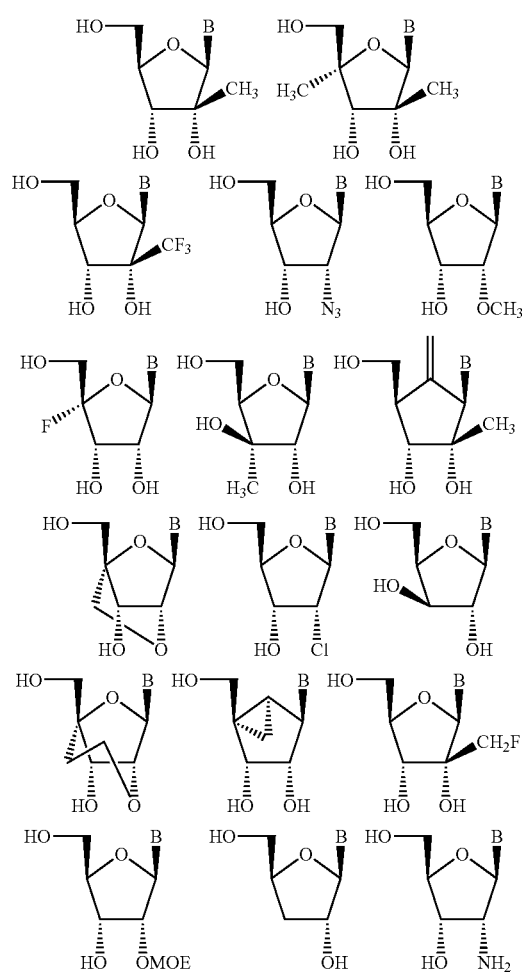

-continued

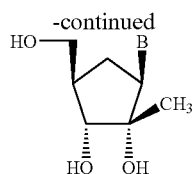

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.) Nucleosides known to be inhibitors/substrates for RNA dependent RNA polymerases (for example HCV NS5B)

In one aspect, the present invention is directed to oligonucleotides that are prepared having enhanced properties compared to native RNA against nucleic acid targets. A target is identified and an oligonucleotide is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonulceotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger et. al., Nucleic Acids Research, 1998, 26, 2473-2480, who pointed out that in considering the furanose conformations which give rise to B-form duplexes consideration should also be given to an O4'-endo pucker contribution.

DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as but not limited to antisense and RNA interference as these mechanisms require the binding of a synthetic oligonucleotide strand to an RNA target strand. In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-$OCH_2CH_2OCH_3$) side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

In all the preceding formulae, the squiggle (~) indicates a bond to an oxygen or sulfur of the 5'-phosphate. Phosphate protecting groups include those described in U.S. Pat. Nos. 5,760,209, 5,614,621, 6,051,699, 6,020,475, 6,326,478, 6,169,177, 6,121,437, 6,465,628 each of which is expressly incorporated herein by reference in its entirety.

Oligomer Synthesis

Oligomerization of modified and unmodified nucleosides is performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition specific protocols for the synthesis of oligomeric compounds of the invention are illustrated in the examples below.

Oligonucleotides are generally prepared either in solution or on a support medium, e.g. a solid support medium. In general a first synthon (e.g. a monomer, such as a nucleoside) is first attached to a support medium, and the oligonucleotide is then synthesized by sequentially coupling monomers to the support-bound synthon. This iterative elongation eventually results in a final oligomeric compound or other polymer such as a polypeptide. Suitable support medium can be soluble or insoluble, or may possess variable solubility in different solvents to allow the growing support bound polymer to be either in or out of solution as desired. Traditional support medium such as solid support media are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489-510).

The term support medium is intended to include all forms of support known to one of ordinary skill in the art for the synthesis of oligomeric compounds and related compounds such as peptides. Some representative support medium that are amenable to the methods of the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support medium, polyethylene glycol PEG's (see Bonora et al., Organic Process Research & Development, 2000, 4, 225-231).

Further support medium amenable to the present invention include without limitation PEPS support a polyethylene (PE) film with pendant long-chain polystyrene (PS) grafts (molecular weight on the order of $10^6$, (see Berg, et al., J. Am. Chem. Soc., 1989, 111, 8024 and International Patent Application WO 90/02749),). The loading capacity of the film is as high as that of a beaded matrix with the additional flexibility to accommodate multiple syntheses simultaneously. The PEPS film may be fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. Also, experiments with other geometries of the PEPS polymer such as, for example, non-woven felt, knitted net, sticks or microwell-plates have not indicated any limitations of the synthetic efficacy.

Further support medium amenable to the present invention include without limitation particles based upon copolymers of dimethylacrylamide cross-linked with N,N'-bisacryloyl-ethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl safcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., J. Am. Chem. Soc., 1975, 97, 6584, Bioorg. Chem. 1979, 8, 351, and J. C. S. Perkin I 538 (1981)).

Further support medium amenable to the present invention include without limitation a composite of a resin and another material that is also substantially inert to the organic synthesis reaction conditions employed. One exemplary composite (see Scott, et al., *J. Chrom. Sci.*, 1971, 9, 577) utilizes glass particles coated with a hydrophobic, cross-linked styrene polymer containing reactive chloromethyl groups, and is supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243 and van Rietschoten in *Peptides* 1974, Y. Wolman, Ed., Wiley and Sons, New York, 1975, pp. 113-116). Contiguous solid support media other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345). Acrylic acid-grafted polyethylene-rods and 96-microtiter wells to immobilize the growing peptide chains and to perform the compartmentalized synthesis. (Geysen, et al., *Proc. Natl. Acad. Sci. USA*, 1984, 81, 3998). A "tea bag" containing traditionally-used polymer beads. (Houghten, *Proc. Natl. Acad. Sci. USA*, 1985, 82, 5131). Simultaneous use of two different supports with different densities (Tregear, *Chemistry and Biology of Peptides*, J. Meienhofer, ed., Ann Arbor Sci. Publ., Ann Arbor, 1972 pp. 175-178). Combining of reaction vessels via a manifold (Gorman, *Anal. Biochem.*, 1984, 136, 397). Multicolumn solid-phase synthesis (e.g., Krchnak, et al., *Int. J. Peptide Protein Res.*, 1989, 33, 209), and Holm and Meldal, in "Proceedings of the 20th European Peptide Symposium", G. Jung and E. Bayer, eds., Walter de Gruyter & Co., Berlin, 1989 pp. 208-210). Cellulose paper (Eichler, et al., *Collect. Czech. Chem. Commun.*, 1989, 54, 1746). Support mediumted synthesis of peptides have also been reported (see, *Synthetic Peptides. A User's Guide*, Gregory A. Grant, Ed. Oxford University Press 1992; U.S. Pat. Nos. 4,415,732; 4,458,066; 4,500,707; 4,668,777; 4,973,679; 5,132,418; 4,725,677 and Re-34,069.)

Support bound oligonucleotide synthesis relies on sequential addition of nucleotides to one end of a growing chain. Typically, a first nucleoside (having protecting groups on any exocyclic amine functionalities present) is attached to an appropriate glass bead support and nucleotides bearing the appropriate activated phosphite moiety, i.e. an "activated phosphorous group" (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re-34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The term "solid support tether," as used herein is generally a di-functional group, covalently binds the ultimate 3'-nucleoside (and thus the nascent oligonucleotide) to the solid support medium during synthesis, but which is cleaved under conditions orthogonal to the conditions under which the 5'-protecting group, and if applicable any 2'-protecting group, are removed. Suitable solid support tethers include, but are not limited to, a divalent group such as alkylene, cycloalkylene, arylene, heterocyclyl, heteroarylene, and the other variables are as described above. Exemplary alkylene tethers include, but are not limited to, $C_1$-$C_{12}$ alkylene (e.g. preferably methylene, ethylene (e.g. ethyl-1,2-ene), propylene (e.g. propyl-1,2-ene, propyl-1,3-ene), butylene, (e.g. butyl-1,4-ene, 2-methylpropyl-1,3-ene), pentylene, hexylene, heptylene, octylene, decylene, dodecylene), etc. Exemplary cycloalkylene groups include $C_3$-$C_{12}$ cycloalkylene groups, such as cyclopropylene, cyclobutylene, cyclopentanyl-1,3-ene, cyclohexyl-1,4-ene, etc. Exemplary arylene tethers include, but are not limited to, mono- or bicyclic arylene groups having from 6 to about 14 carbon atoms, e.g. phenyl-1,2-ene, naphthyl-1,6-ene, napthyl-2,7-ene, anthracenyl, etc. Exemplary heterocyclyl groups within the scope of the invention include mono- or bicyclic aryl groups having from about 4 to about 12 carbon atoms and about 1 to about 4 hetero atoms, such as N, O and S, where the cyclic moieties may be partially dehydrogenated. Certain heteroaryl groups that may be mentioned as being within the scope of the invention include: pyrrolidinyl, piperidinyl (e.g. 2,5-piperidinyl, 3,5-piperidinyl), piperazinyl, tetrahydrothiophenyl, tetrahydrofuranyl, tetrahydro quinolinyl, tetrahydro isoquinolinyl, tetrahydroquinazolinyl, tetrahydroquinoxalinyl, etc. Exemplary heteroarylene groups include mono- or bicyclic aryl groups having from about 4 to about 12 carbon atoms and about 1 to about 4 hetero atoms, such as N, O and S. Certain heteroaryl groups that may be mentioned as being within the scope of the invention include: pyridylene (e.g. pyridyl-2,5-ene, pyridyl-3,5-ene), pyrimidinyl, thiophenyl, furanyl, quinolinyl, isoquinolinyl, quinazolinyl, quinoxalinyl, etc.

Suitable reagents for introducing the group HOCO-Q-CO include diacids ($HO_2C$-Q-$CO_2H$). Particularly suitable diacids include malonic acid (Q is methylene), succinic acid (Q is 1,2-ethylene), glutaric acid, adipic acid, pimelic acid, and phthalic acid. Other suitable reagents for introducing HOCO-Q-CO above include diacid anhydrides. Particularly suitable diacid anhydrides include malonic anhydride, succinic anhydride, glutaric anhydride, adipic anhydride, pimelic anhydride, and phthalic anhydride. Other suitable reagents for introducing HOCO-Q-CO include diacid esters, diacid halides, etc. One especially preferred reagent for introducing HOCO-Q-CO is succinic anhydride.

The compound of formula may be linked to a support via terminal carboxylic acid of the HOCO-Q-CO group, via a reactive group on the support medium. In some embodiments, the terminal carboxylic acid forms an amide linkage with an amine reagent on the support surface. In other embodiments, the terminal carboxylic acid forms an ester with an OH group on the support medium. In some embodiments, the terminal carboxylic acid may be replaced with a terminal acid halide, acid ester, acid anhydride, etc. Specific acid halides include carboxylic chlorides, bromides and iodides. Specific esters include methyl, ethyl, and other $C_1$-$C_{10}$ alkyl esters. Specific anhydrides include formyl, acetyl, propanoyl, and other $C_1$-$C_{10}$ alkanoyl esters.

The present invention also encompasses the preparation of oligomeric compounds incorporating at least one 2'-O-protected nucleoside into the oligomeric compounds delineated herein. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound. All 2'-O— protecting groups amenable to the synthesis of oligomeric compounds are included in the present invention. In general, a protected nucleoside is attached to a solid support by for example a succinate linker. Then the oligonucleotide is elongated by repeated cycles of deprotecting the 5'-terminal hydroxyl group, coupling of a further nucleoside unit, capping and oxidation (alternatively sulfurization). In a more frequently used method of synthesis the completed oligonucleotide is cleaved from the solid support with the removal of phosphate protecting groups and exocyclic amino protecting groups by treatment with an ammonia solution. Then a further deprotection step is normally required for the more specialized protecting groups used for the protection of 2'-hydroxyl groups which will give the fully deprotected oligonucleotide.

A large number of 2'-O-protecting groups have been used for the synthesis of oligoribonucleotides but over the years more effective groups have been discovered. The key to an effective 2'-O-protecting group is that it is capable of selectively being introduced at the 2'-O-position and that it can be removed easily after synthesis without the formation of unwanted side products. The protecting group also needs to be inert to the normal deprotecting, coupling, and capping steps required for oligoribonucleotide synthesis. Some of the protecting groups used initially for oligoribonucleotide synthesis included tetrahydropyran-1-yl and 4-methoxytetrahydropyran-4-yl. These two groups are not compatible with any 5'-O-protecting groups so modified versions were used with 5'-DMT groups such as 1-(2-fluorophenyl)-4-methoxypiperidin-4-yl (Fpmp). Reese has identified a number of piperidine derivatives (like Fpmp) that are useful in the synthesis of oligoribonucleotides including 1-[(chloro-4-methyl)phenyl] 4'-methoxypiperidin-4-yl (Reese et al., Tetrahedron Lett., 1986, (27), 2291). Another approach was to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group initially used for the synthesis of oligoribonucleotides was the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal such as for example the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, (55), 320-324.) The group examined fluoride labile and photolabile protecting groups that are removed using moderate conditions. One photolabile group that was examined was the [2-(nitrobenzyl) oxy]methyl (nbm) protecting group (Schwartz et al., Bioorg. Med. Chem. Lett., 1992, (2), 1019.) Other groups examined included a number structurally related formaldehyde acetal-derived, 2'-O-protecting groups. Also prepared were a number of related protecting groups for preparing 2'-O-alkylated nucleoside phosphoramidites including 2'-O-[(triisopropylsilyl)oxy]methyl (2'-O—$CH_2$—O—$Si(iPr)_3$, TOM). One 2'-O-protecting group that was prepared to be used orthogonally to the TOM group was 2'-O—[(R)-1-(2-nitrophenyl)ethyloxy) methyl] ((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

Although a lot of research has focused on the synthesis of oligoribonucleotides the main RNA synthesis strategies that are presently being used commercially include 5'-O-DMT-2'-O-t-butyldimethylsilyl (TBDMS), 5'-O-DMT-2'-O-[1 (2-fluorophenyl)-4-methoxypiperidin-4-yl] (FPMP), 2'-O-[(triisopropylsilyl)oxy]methyl (2'-O—$CH_2$—O—$Si(iPr)_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present invention.

The primary groups being used for commercial RNA synthesis are:
TBDMS=5'-O-DMT-2'-O-t-butyldimethylsilyl;
TOM=2'-O-[(triisopropylsilyl)oxy]methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-[1 (2-fluorophenyl)$_4$-methoxypiperidin-4-yl].

All of the aforementioned RNA synthesis strategies are amenable to the present invention. Strategies that would be a hybrid of the above e.g. using a 5'-protecting group from one strategy with a 2'-O-protecting from another strategy is also amenable to the present invention.

Targets of the Invention

"Targeting" an antisense oligomeric compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid. The terms region, segment, and site can also be used to describe an oligomeric compound of the invention such as for example a gapped oligomeric compound having 3 separate segments.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense oligomeric compounds of the present invention.

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also suitable to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also suitable target sites. mRNA transcripts produced via the process of splicing of two (or more) mRNAs from different gene sources are known as "fusion transcripts". It is also known that introns can be effectively targeted using antisense oligomeric compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequences.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also suitable target nucleic acids.

The locations on the target nucleic acid to which the antisense oligomeric compounds hybridize are hereinbelow referred to as "suitable target segments." As used herein the term "suitable target segment" is defined as at least an 8-nucleobase portion of a target region to which an active antisense oligomeric compound is targeted. While not wishing to be bound by theory, it is presently believed that these target segments represent portions of the target nucleic acid which are accessible for hybridization.

Exemplary antisense oligomeric compounds include oligomeric compounds that comprise at least the 8 consecutive nucleobases from the 5'-terminus of a targeted nucleic acid e.g. a cellular gene or mRNA transcribed from the gene (the remaining nucleobases being a consecutive stretch of the same oligonucleotide beginning immediately upstream of the 5'-terminus of the antisense compound which is specifically hybridizable to the target nucleic acid and continuing until the oligonucleotide contains from about 8 to about 80 nucleobases). Similarly, antisense oligomeric compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains from about 8 to about 80 nucleobases). One having skill in the art armed with the antisense compounds illustrated herein will be able, without undue experimentation, to identify further antisense compounds.

Once one or more target regions, segments or sites have been identified, antisense oligomeric compounds are chosen which are sufficiently complementary to the target, i.e., hybridize sufficiently well and with sufficient specificity, to give the desired effect.

In accordance with one embodiment of the present invention, a series of nucleic acid duplexes comprising the antisense oligomeric compounds of the present invention and their complements can be designed for a specific target or targets. The ends of the strands may be modified by the addition of one or more natural or modified nucleobases to form an overhang. The sense strand of the duplex is then designed and synthesized as the complement of the antisense strand and may also contain modifications or additions to either terminus. For example, in one embodiment, both strands of the duplex would be complementary over the central nucleobases, each having overhangs at one or both termini.

For example, a duplex comprising an antisense oligomeric compound having the sequence CGAGAGGCGGACGG-GACCG (SEQ ID NO:1) and having a two-nucleobase overhang of deoxythymidine(dT) would have the following structure:

RNA strands of the duplex can be synthesized by methods disclosed herein or purchased from various RNA synthesis companies such as for example Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of the buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA compound is 20 uM. This solution can be stored frozen (−20° C.) and freeze-thawed up to 5 times.

Once prepared, the desired synthetic duplexes are evaluated for their ability to modulate target expression. When cells reach 80% confluency, they are treated with synthetic duplexs comprising at least one oligomeric compound of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired dsRNA compound at a final concentration of 200 nM. After 5 hours of treatment, the medium is replaced with fresh medium. Cells are harvested 16 hours after treatment, at which time RNA is isolated and target reduction measured by RT-PCR.

In a further embodiment, the "suitable target segments" identified herein may be employed in a screen for additional oligomeric compounds that modulate the expression of a target. "Modulators" are those oligomeric compounds that decrease or increase the expression of a nucleic acid molecule encoding a target and which comprise at least an 8-nucleobase portion which is complementary to a suitable target segment. The screening method comprises the steps of contacting a suitable target segment of a nucleic acid molecule encoding a target with one or more candidate modulators, and selecting for one or more candidate modulators which decrease or increase the expression of a nucleic acid molecule encoding a target. Once it is shown that the candidate modulator or modulators are capable of modulating (e.g. either decreasing or increasing) the expression of a nucleic acid molecule encoding a target, the modulator may then be employed in further investigative studies of the function of a target, or for use as a research, diagnostic, or therapeutic agent in accordance with the present invention.

The suitable target segments of the present invention may also be combined with their respective complementary antisense oligomeric compounds of the present invention to form stabilized double-stranded (duplexed) oligonucleotides.

Hybridization

In the context of this invention, "hybridization" means the pairing of complementary strands of oligomeric compounds. In the present invention, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense oligomeric compound is specifically hybridizable when binding of the compound to the target nucleic acid interferes with the normal function of the target nucleic acid to cause a loss of activity, and there is a sufficient degree of complementarity to avoid non-specific binding of the antisense oligomeric compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). The antisense oligomeric compounds of the present invention can comprise at least about 70%, at least about 80%, at least about 90%, at least about 95%, or at least about 99% sequence complementarity to a target region within the target nucleic acid sequence to which they are targeted. For example, an antisense oligomeric compound in which 18 of 20 nucleobases of the antisense oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Screening and Target Validation

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present invention.

The suitable target segments of the present invention may also be combined with their respective complementary antisense oligomeric compounds of the present invention to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds of the present invention can also be applied in the areas of drug discovery and target validation. The present invention comprehends the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

Kits, Research Reagents, Diagnostics, and Therapeutics

The oligomeric compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the oligomeric compounds of the present invention, either alone or in combination with other oligomeric compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense oligomeric compounds are compared to control cells or tissues not treated with antisense oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

The oligomeric compounds of the invention are useful for research and diagnostics, because these oligomeric compounds hybridize to nucleic acids encoding proteins. For example, oligonucleotides that are shown to hybridize with such efficiency and under such conditions as disclosed herein as to be effective protein inhibitors will also be effective primers or probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

The specificity and sensitivity of antisense is also harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense oligomeric compounds can be useful therapeutic modalities that can be configured to be useful in treatment regimes for the treatment of cells, tissues and animals, especially humans.

For therapeutics, an animal, such as a human, suspected of having a disease or disorder which can be treated by modulating the expression of a selected protein is treated by administering antisense oligomeric compounds in accordance with this invention. For example, in one non-limiting embodiment, the methods comprise the step of administering to the animal in need of treatment, a therapeutically effective amount of a protein inhibitor. The protein inhibitors of the present invention effectively inhibit the activity of the protein or inhibit the expression of the protein. In some embodiments, the activity or expression of a protein in an animal or cell is inhibited by at least about 10%, at least about 20%, at least about 30%, at least about 40%, at least about 50%, at least about 60%, at least about 70%, at least about 80%, at least about 90%, at least about 95%, at least about 99%, or by 100%.

For example, the reduction of the expression of a protein may be measured in serum, adipose tissue, liver or any other body fluid, tissue or organ of the animal. The cells contained within the fluids, tissues or organs being analyzed can contain a nucleic acid molecule encoding a protein and/or the protein itself.

The oligomeric compounds of the invention can be utilized in pharmaceutical compositions by adding an effective amount of an oligomeric compound to a suitable pharmaceutically acceptable diluent or carrier. Use of the oligomeric compounds and methods of the invention may also be useful prophylactically.

In another embodiment, the present invention provides for the use of a compound(s) of the invention in the manufacture of a medicament for the treatment of any and all diseases and conditions disclosed herein.

Formulations

The antisense oligomeric compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the oligomeric compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the oligomeric compounds of the invention: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860, which is incorporated herein in its entirety.

EXAMPLES

The compounds and processes of the present invention will be described further in detail with respect to specific preferred embodiments by way of examples, it being understood that these are intended to be illustrative only and not limiting of the scope of the invention. Various changes and modifications to the disclosed embodiments will be apparent to those skilled in the art and such changes and modifications including, without limitation, those relating to the chemical structures,

Example 1

Synthesis of Peptide Nucleic Acid (PNA)-Peptide Conjugates Containing an Activated Disulfide.

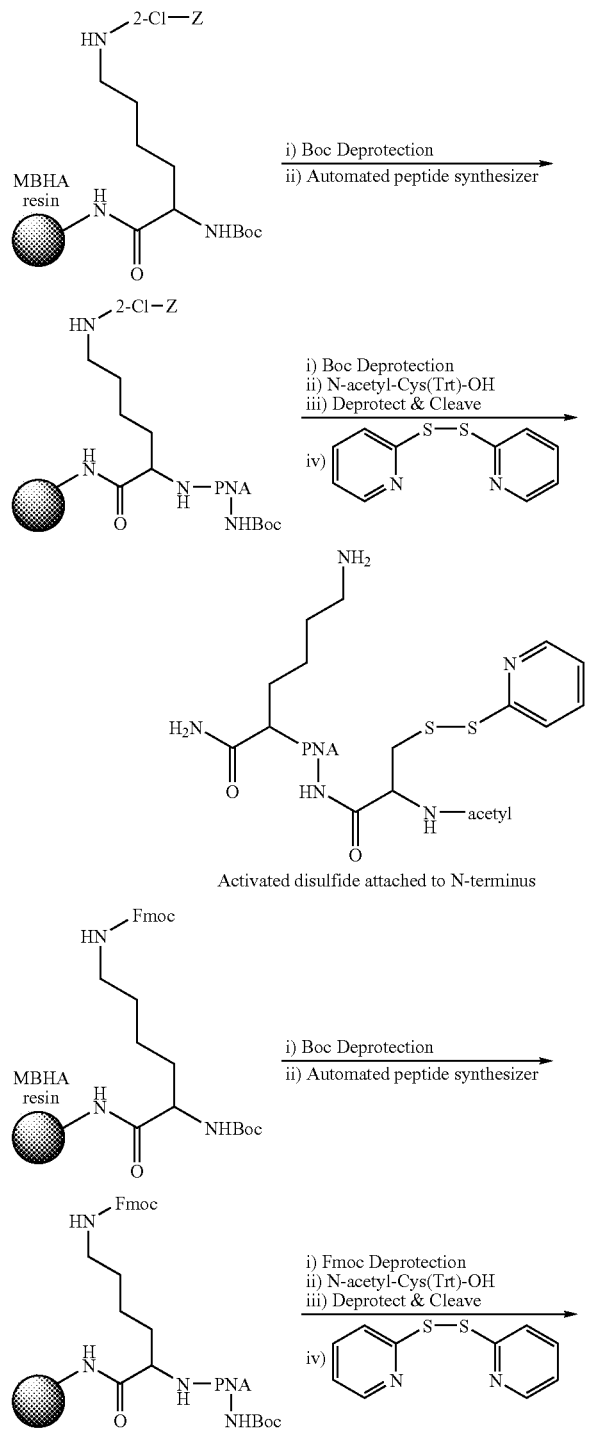

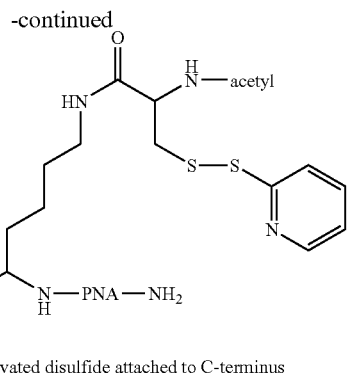

Activated disulfide attached to C-terminus

The PNA part of the conjugates was assembled using an automated 433 A peptide synthesizer (Applied Biosystems) and commercially available tert-butyloxycarbonyl/benzyloxycarbonyl (Boc/Cbz) protected PNA monomers (Applied Biosystems) according to previously published procedures for PNA synthesis (Boc chemistry) (See L. Christensen, et al. (1995), *J. Pept. Sci.* 1, 175-183; T. Koch, et al. (1997), *J. Pept. Res.* 49, 80-88.). The synthesis was performed on MBHA LL polystyrene resin (NovaBiochem), pre-loaded to about 0.1-0.2 mmol/g with either Boc-Lys(2-Cl-Z)-OH (NovaBiochem) for N-terminal modification or Boc-Lys(Fmoc)-OH (NovaBiochem) for modification of the C-terminal Lys.

The synthesis of the peptide part of the conjugate was carried out by continuing the synthesis on the N-terminus of the PNA according to standard procedures for solid phase peptide synthesis. The thiol functionality was introduced according to standard procedures for solid phase peptide synthesis using N-acetyl-Cys(Trt)-OH or any other carboxylic acid containing a suitably protected thiol after removing either the Fmoc group at the C-terminal Lys or the Boc group of the N-terminus of the PNA-peptide conjugate. For final deprotection and cleavage one vol. of TFA/TFMSA/thioanisol/m-cresol (8:1:1:1) was added and the suspension was shaken for 1.5-6 h. The filtrate was then added to a 10-fold volume of cold diethylether, mixed and centrifuged. The supernatant was removed and the pellet was re-suspended in ether. This was repeated three times. The pellet was dried and re-dissolved in degassed water/pyridine (8:2) before 10 equiv. of 2,2-dipyridyl-disulfide in acetonitrile (ca. 0.02-0.1 M) was added to form the activated disulfide (Scheme 1). The pH of the mixture was adjusted to pH 8.5-9.0 with aqueous TEA and the mixture was shaken for ca. 3-6 h. After evaporation of the solvents in vacuo, the residue was dissolved in water and washed with ether to remove the excess dithiodipyridine. After ether removal, purification was performed on a Gilson HPLC system (215 liquid handler, 155 UV/VIS and 321 pump), by reverse phase high performance liquid chromatography (RP-HPLC), using a Zorbax (C-3, 5 µm, 300 Å, 250× 7.8 mm, 4 mL/min). A linear gradient from solvent A: 0.1% heptafluorobutyric acid in water to B: acetonitrile was used as the liquid phase. Product-containing fractions were combined and purity was determined by analytical HPLC and composition confirmed by electrospray mass spectrometry. Samples were lyophilized and stored at −20° C. until before use. Representative examples of PNAs, which carry the dithiopyridine functionality at their C- or their N-terminus, are listed in Table 1.

TABLE 1

Examples of PNAs containing the activated disulfide functionality.

| ISIS # | Sequence | $MW_{calc}$ | $MW_{ob}$ | SEQ ID NO: |
|---|---|---|---|---|
| 347349 | KKOrnKKOrnKK-CACAGATGACATTAG-K($R^1$) | 5620 | 5617 | SEQ ID NO: 4 |
| 350126 | $(dK)_8$-CACAGATGACATTAG-K($R^2$) | 5675 | 5673 | SEQ ID NO: 5 |
| 350226 | $(dK)_8$-CACAGATGACATTAG-K($R^1$) | 5647 | 5645 | SEQ ID NO: 6 |
| 358346 | $R^1$-$(dK)_8$-CACAGATGACATTAG-K | 5620 | 5617 | SEQ ID NO: 7 |
| 368640 | $R^1$-$(dK)_8$-CACAGATGACATTAG-K(Bio) | 6019 | 6017 | SEQ ID NO: 8 |

Where: Orn = L-ornithine and dK = D-lysine

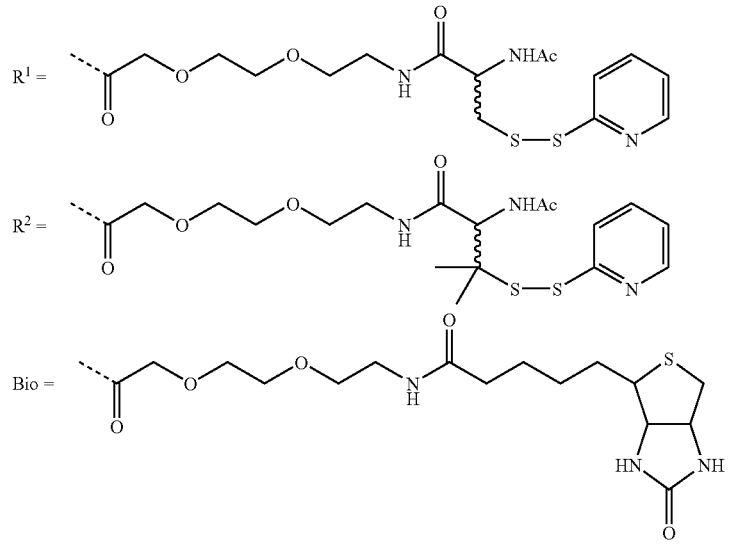

Example 2

Synthesis of ISIS367745

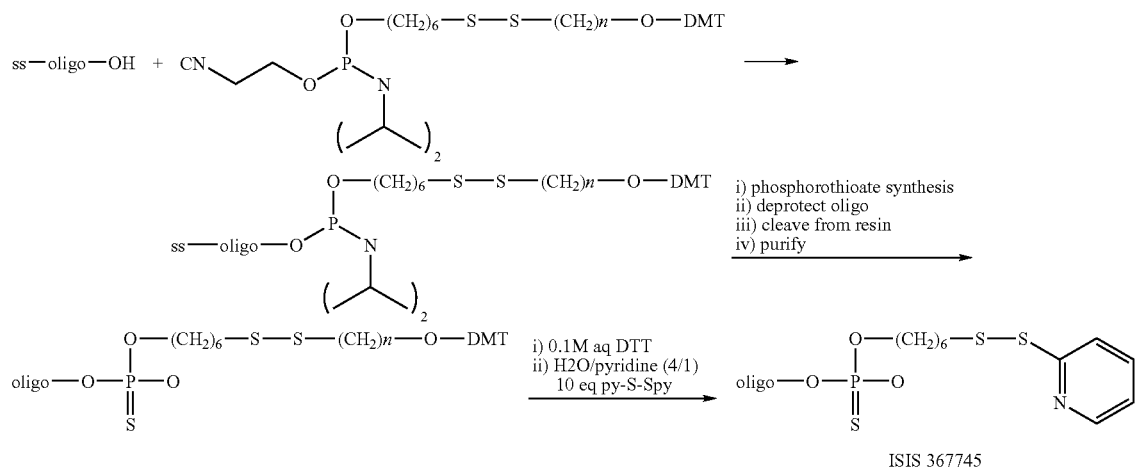

The oligonucleotide was assembled using phosphoramidite chemistry according to standard procedures known to one of ordinary skill in the art for solid phase synthesis of oligonucleotides. A suitably protected disulfide containing phosphoramidite was coupled to the 5'-end of the oligonucleotide on resin, using standard phosphoramidite chemistry (see above scheme).

After final deprotection and cleavage from the resin, the disulfide-modified oligonucleotide was purified by reversed phase HPLC and the thiol was generated by adding a 0.1 M aqueous solution of DTT according to manufacturer's protocol. The oligonucleotide was passed through a size exclusion column (Sephadex G25) to separate from excess DTT and the product-containing fractions were combined and evaporated. The oligonucleotide was then re-dissolved in degassed water/pyridine (80:20) and a solution of 10 equiv. 2,2-dipyridyl-disulfide in acetonitrile (ca. 0.02-0.1 M) was added. The pH of the mixture was adjusted to pH 8.5-9.0 with aqueous TEA and the mixture was shaken for ca. 3-6 h. After evaporation of the solvents in vacuo, the residue was dissolved in water and purified by size exclusion chromatography (Sephadex G25) followed by reversed phase HPLC. The product-containing fractions were combined and evaporated in vacuo and the compound was stored at −20° C. until use.

ISIS367745(SEQ ID NO:9) —an oligonucleotide containing an activated disulfide at the 5'-End After final deprotection and cleavage from the resin, the modified oligonucleotide is purified by reversed phase HPLC and the thiol generated using relevant, standard deprotection conditions. The thiol-modified oligonucleotide is purified and dissolved in degassed water/pyridine (80:20) to which a solution of 10 equiv. 2,2-dipyridyl-disulfide in acetonitrile (ca. 0.02-0.1 M) is added. The pH of the mixture is adjusted to pH 8.5-9.0 with aqueous TEA and the mixture is shaken for

| Isis # | Sequence/Modification | MW$_{calc}$ | MW$_{ob}$ | |
|---|---|---|---|---|
| 367745 | X-CTGCTAGCCTCTGGATTTGA<br>all PS; _ = 2'-MOE | 7521 | | 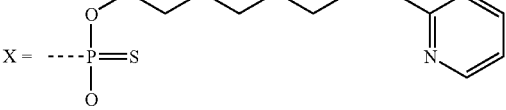 |

Example 3

Synthesis of Oligonucleotides Containing an Activated Disulfide at the 5'-End.

The oligonucleotide is assembled using phosphoramidite chemistry according to standard procedures known to one of skill in the art for solid phase synthesis of oligonucleotides. At the 5'-end, a suitably protected monomer (see below for non-limiting examples) is coupled to the oligonucleotide on the resin using phosphoramidite chemistry.

Exemplified Phosphoramidite Building Blocks for Introducing an Activated Disulfide at the 5'-Terminus of an Oligonucleotide.

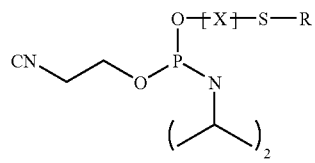

where examples of X include, but are not limited to

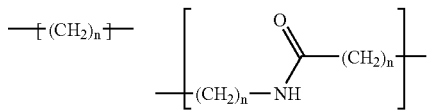

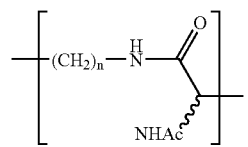

R = thiol protecting group, or S-disulfide protecting group ca. 3-6 h. After evaporation of the solvents in vacuo, the residue is dissolved in water and purified by size exclusion chromatography (Sephadex G25) followed by reversed phase HPLC. The product-containing fractions are combined and evaporated in vacuo and the compound is stored at −20° C. until use.

Example 4

Synthesis of Oligonucleotides Containing an Activated Disulfide at the 3'-End.

A solid support is bound to a spacer group via its free hydroxyl using standard ester formation chemistry, known to one of ordinary skill in the art. The spacer group is comprised of a free hydroxyl, a protected hydroxyl, and a protected sulfide or a protected disulfide. The protected hydroxyl is deprotected and the oligonucleotide is assembled thereon using phosphoramidite chemistry according to standard procedures known to one of ordinary skill in the art in solid phase synthesis of oligonucleotides. After the oligonucleotide has been fully synthesized, spacer-bound or thiol-modified oligonucleotide, is deprotected, cleaved and finally purified by reversed phase HPLC. The thiol is generated using relevant, standard thiol deprotection conditions. The thiol-modified oligonucleotide is purified and dissolved in degassed water/pyridine (80:20) to which a solution of 10 equiv. 2,2-dipyridyl-disulfide in acetonitrile (ca. 0.02-0.1 M) is added. The pH of the mixture is adjusted to pH 8.5-9.0 with aqueous TEA and the mixture is shaken for ca. 3-6 h. After evaporation of the solvents in vacuo, the residue is dissolved in water and purified by size exclusion chromatography (Sephadex G25) followed by reversed phase HPLC. The product-containing fractions are combined and evaporated in vacuo and the compound is stored at −20° C. until use. Examples of spacers which are useful in synthesizing the thiol-modified oligonucleotides of the present invention:

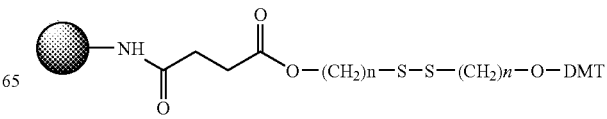

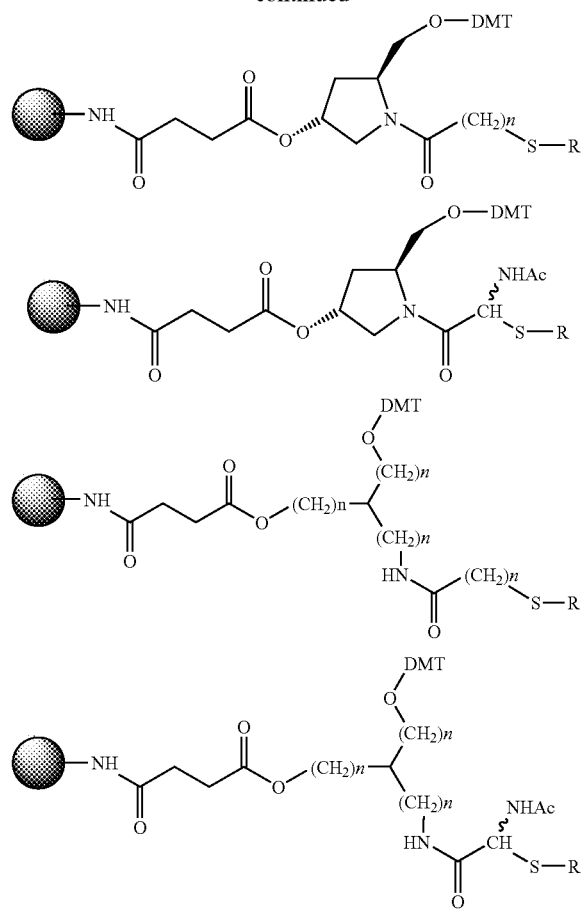

n = 0-10
R = - - -S—Alkyl, 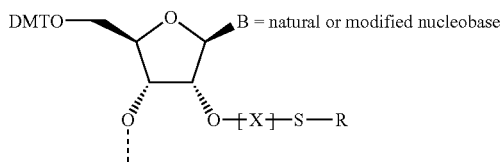

Example 5

Synthesis of Oligonucleotides Containing an Activated Disulfide at the 2' Position.

The oligonucleotide is assembled using phosphoramidite chemistry according to standard procedures known to one of skill in the art for solid phase synthesis of oligonucleotides. A protected thiol or disulfide is introduced within the sequence using a nucleoside phosphoramidite modified at the 2'-position with a suitably protected thiol or disulfide functionality, as indicated below.

where examples of X include, but are not limited to

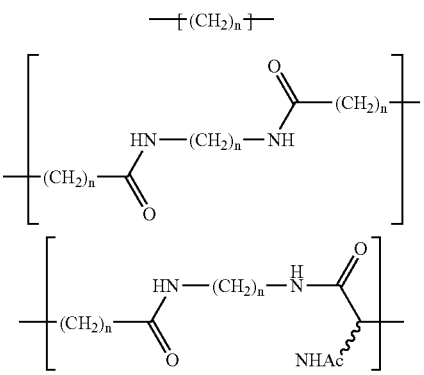

R=thiol protecting group, or S-disulfide protecting group

After final deprotection and cleavage from the resin, the-modified oligonucleotide is purified by reversed phase HPLC and the thiol generated using relevant, standard deprotection conditions. The thiol-modified oligonucleotide is purified and dissolved in degassed water/pyridine (80:20) to which a solution of 10 equiv. 2,2-dipyridyl-disulfide in acetonitrile (ca. 0.02-0.1 M) is added. The pH of the mixture is adjusted to pH 8.5-9.0 with aqueous TEA and the mixture is shaken for ca. 3-6 h. After evaporation of the solvents in vacuo, the residue is dissolved in water and purified by size exclusion chromatography (Sephadex G25) followed by reversed phase HPLC. The product-containing fractions are combined and evaporated in vacuo and the compound is stored at −20° C. until use.

Example 6

Synthesis of siRNA Duplexes Containing Activated Disulfides.

The two complementary sense and antisense strands composed of natural or modified ribonucleotide building blocks are assembled using phosphoramidite chemistry according to standard procedures known to one of skill in the art for solid phase synthesis of oligonucleotides. Activated disulfide groups are incorporated into the oligonucleotide strands, as described herein in examples 3, 4 or 5. Prior to use, the activated disulfide modified oligonucleotide is annealed to its complementary unmodified strand to form the siRNA duplex by mixing equal amounts of both compounds in water or physiological buffer, heating the mixture for ca. 10 min to ca. 90° C. and slowly cooling the mixture to r.t.

Example 7

Protein Binding of Oligomers in Mouse Plasma.

Mouse plasma solutions were prepared by adding 12 μL of a 1 mM aqueous solution of oligomer containing activated disulfides to 1.2 mL of 100% mouse plasma stabilized with 10 mM Hepes. Prior to addition of oligomer, glutathione (GSH: GSSG, 50:1) was added to one of the samples to a final concentration of 10 μM. The samples were incubated at 37° C. for 24.6 h and aliquots (100 μL) were removed for analysis at 0.1, 0.25, 0.5, 1.0, 2.25, 4.0, 7.5, 24.0 and 24.6 h. At 24.1 h GSH was added to the solutions to a final conc. of 5 mM and incubated for an additional 0.5 h. The last aliquot used for protein binding analysis was removed at 24.6 h. For HPLC analysis, 200 µL of 10% dichloroacetic acid in H$_2$O:AcCN (5:1) was added to each aliquot and the precipitated plasma proteins were removed by centrifugation. 200 µL of supernatant was carefully removed, 12 µL of the standard solution was added (PNA 6-mer, 0.1 mM aqueous solution) and the samples were subjected to HPLC analysis. (Zorbax 300 SB C$_3$ column at 60° C.; eluent A: 0.1% aq. HFBA, B: CH$_3$CN; gradient: 0-60 in 30 min.). For further details please see 1) Bellomo, G.; Vairetti, M.; Stivala, L.; Mirabelli, F.; Richelmi, P. et al. Demonstration of nuclear compartmentalization of glutathione in hepatocytes. *Proc Natl Acad Sci USA* 1992, 89, 4412-4416; or 2) Martinovich, G. G.; Cherenkevich, S. N.; Sauer, H. Intracellular redox state: towards quantitative description. *Eur Biophys J* 2005.

Example 8

Bio-Reversible Protein Binding of Oligomer Containing Activated Disulfides in Mouse Plasma.

Figures 2, 2A:
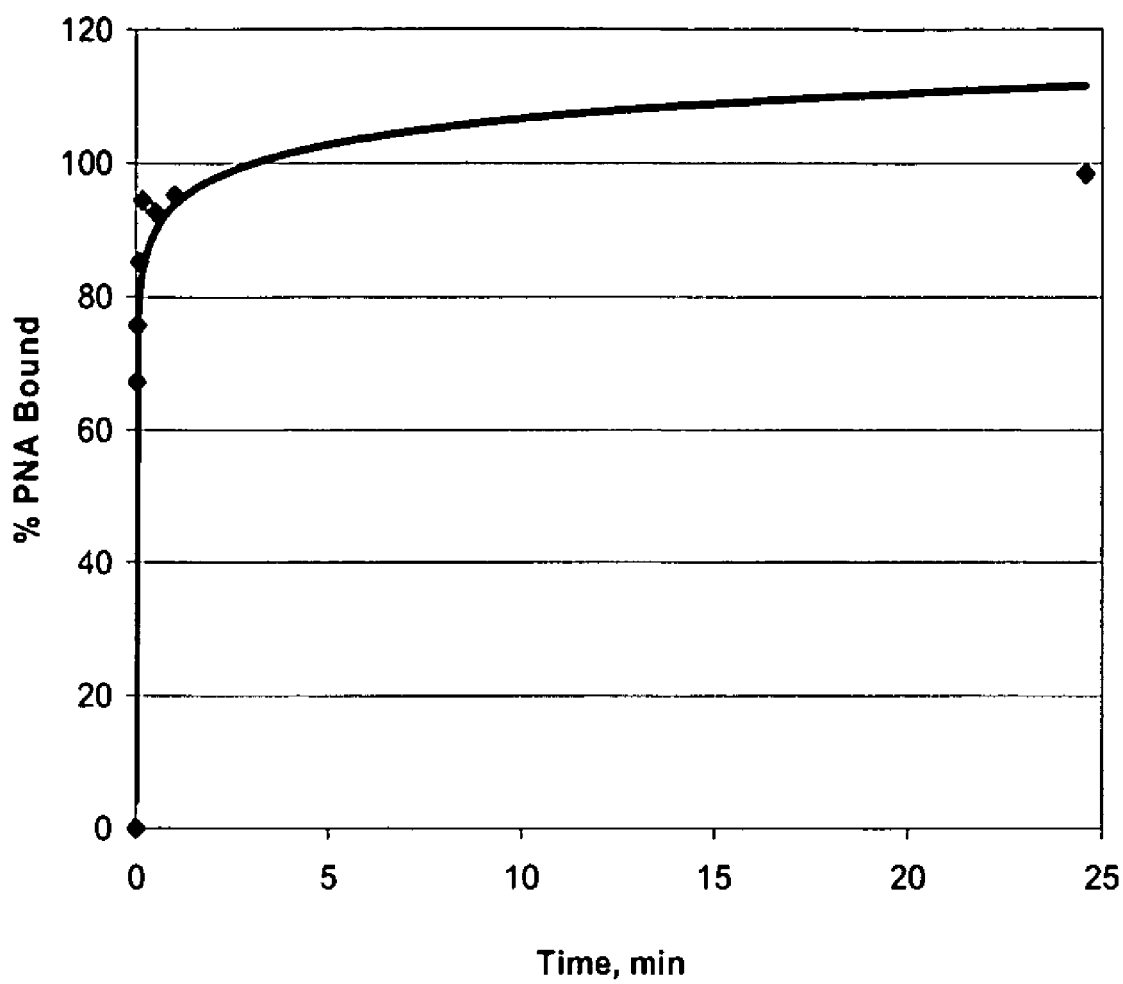
FIG. 2 2a) is a graphical analysis of the results of the plasma protein binding experiment for ISIS350226 in the absence and in the presence of added glutathione; 2b) depicts release of ISIS350226 from the plasma proteins was facilitated by the addition of 5 mM glutathione (a concentration similar to that inside a cell) as described herein in Example 7; 2c) depicts a similar experiment was carried out where the release of the PNA-peptide conjugate using 5 mM GSH was monitored over time as shown in FIG. 2c.
Figure 2B:
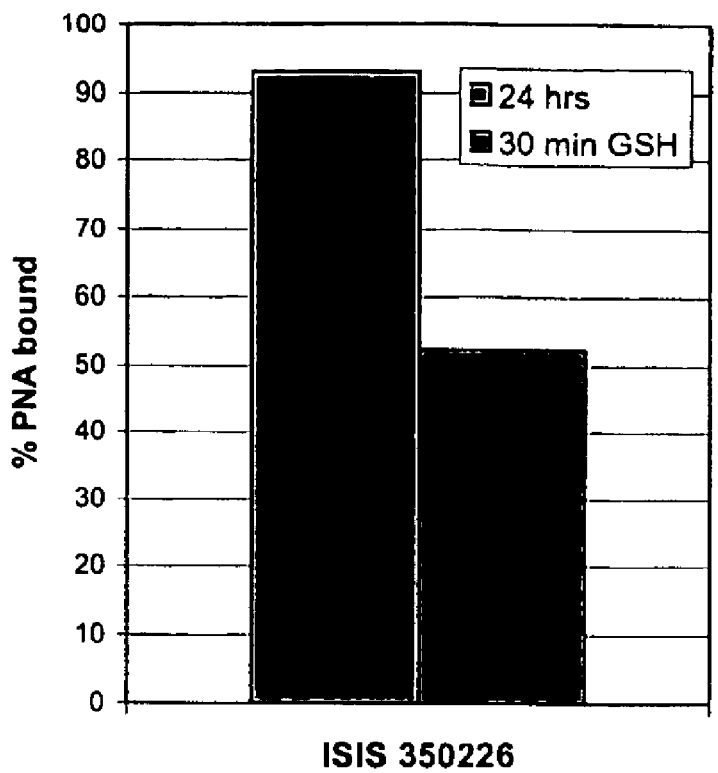
Figure 2C:
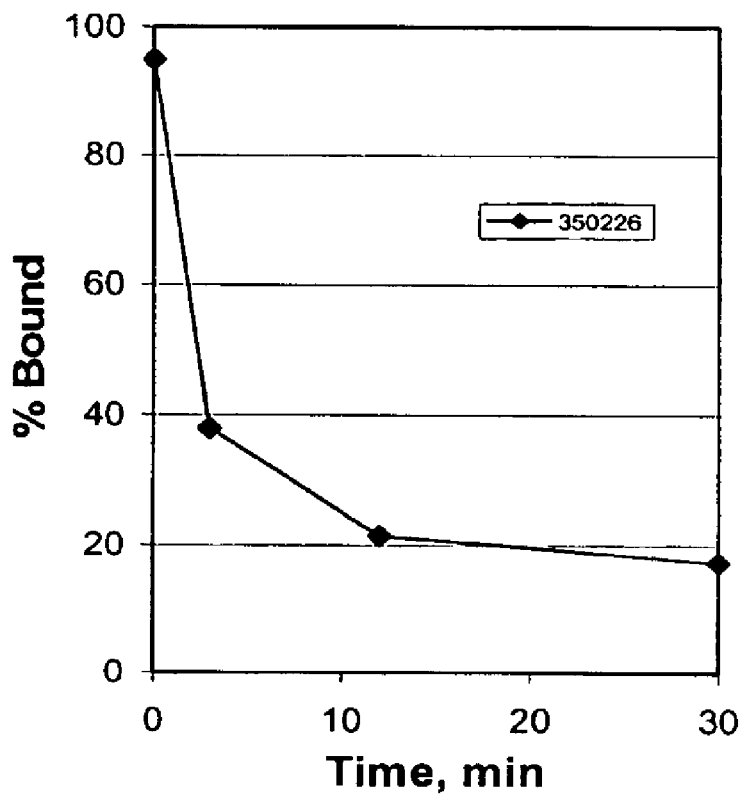

In one embodiment of the invention ISIS350226, a PNA-peptide conjugate, containing an activated disulfide, was examined for protein binding, as described herein in Example 7. A graphical analysis of the results of this experiment is shown in FIG. 2a. As shown in FIG. 2a the PNA conjugate remains attached to the plasma proteins for over 24 h. Release of the PNA-peptide conjugate from the plasma proteins was facilitated by the addition of 5 mM glutathione (a concentration similar to that inside a cell) as described herein in Example 7. A graphical analysis of the result of this experiment is shown in FIG. 2b. A similar experiment was carried out where the release of the PNA-peptide conjugate using 5 mM GSH was monitored over time as shown in FIG. 2c. These data indicate that the reductive environment inside the cell will release the PNA from the plasma proteins. Therefore, an embodiment of the invention is an activated oligomer which is capable of forming a bio-reversible bond with plasma proteins, i.e. the activated oligomer is bound to plasma proteins under plasma conditions, however become released under cellular conditions.

Example 9

Effect of Mouse Plasma Protein Binding on Enzymatic Stability of Oligomeric Compounds.

Oligomeric compounds were incubated with mouse plasma (100%) at 37° C., at a concentration of 10 µM. At certain time points an aliquot was removed from the incubating stock solution. Reduced glutathione (GSH) was immediately added to the aliquot to yield a GSH concentration of 10 mM. The aliquot was incubated at 37° C. for 15 min and then added to double the volume of a 10% dichloroacetic acid solution in water:acetonitrile (5:1). The precipitate was spun down by centrifugation and ⅔ of the supernatant was transferred to a test tube for HPLC analysis. A standard was added to the test tube for quantification purposes. The degradation of the peptide portion of the conjugate was measured as the percent of the full length parent compound as a function of time by HPLC.

Example 10

Effect of Mouse Plasma Protein Binding on Enzymatic Stability of Oligomers Containing Activated Disulfides.

In one embodiment of the invention, two oligomers, ISIS347349, a peptide-PNA conjugate containing an activated disulfide and ISIS 309145, a peptide-PNA conjugate control containing no activated disulfide, were examined for the effect of mouse plasma protein binding on enzymatic stability, as described herein in example 9. Graphical analyses of the results of these experiments are shown in FIG. 3.

Example 11

Radiolabeling of PNA-peptide conjugate Isis 358346 with $^3$H-acetylchloride.

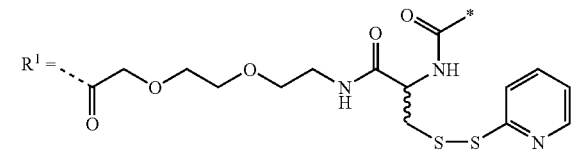

R$^1$-dK)$_8$—CACAGATGACATTAG-K (SEQ ID NO 10)

The PNA-peptide conjugate Isis 358346 was synthesized by Boc chemistry on MBHA resin pre-loaded with Boc-Lys (Fmoc)-OH as described herein in example 1. Subsequently, the Fmoc-protection was removed from the C-terminal Lys side chain with piperidine in DMF according to standard procedures. The resin was then washed with DMF and DCM and dried in vacuo. Custom radiolabeling of the compounds was carried out at Moravek Biochemicals as follows.

The resin was placed into a small custom made synthesis column equipped with a glass frit, a stop cock and an argon inlet and allowed to swell in DCM for 2 h. After removal of the solvent, a mixture of 5.0 equiv. acetylchloride (methyl, $^3$H) and 15 equiv. N,N-diisopropylethylamine (DIEA) in 300 µL dry DCM was added and allowed to react for 1 h under frequent mixing. The resin was washed with DCM, pyridine and again with DCM and a mixture of 2% acetic anhydride in anhydrous pyridine/DMF was added to the resin and allowed to react for 10 min under frequent mixing. This step was repeated twice and the resin was washed thoroughly with pyridine, DMF and DCM. Finally, the compound was deprotected, cleaved from resin, converted to the dithiopyridine derivative and purified by reversed phase HPLC purification according to the conditions as described herein in example 1. The purified compound was converted to the chloride salt using a Dowex anion exchange resin (Dowex 2×8-200, Aldrich 428639 converted to Cl-form). All sample-containing fractions were combined and evaporated. The sample was finally redissolved in 25% aqueous EtOH and stored frozen until use.

Example 12

PK/Tissue Distribution Studies in Balb/c Mice.

Radiolabeled oligomeric compounds, either free or prebound to mouse plasma, were administered by i.v. tail vein injection into Male Balb/c mice (n=3 per time point per compound) at a dose of 3 mg/kg (0.5 mg/mL in PBS with 3%

EtOH, pH 7.1). Mice were sacrificed after 4, 24 and 48 hours and samples from blood, feces, urine, heart, lung, liver, kidney, spleen, mesentery lymph nodes, pancreas, small/large intestine, colon, testes, skeleton muscle and furless skin were collected and dissolved in tissue solubilizer. The samples were then added to liquid scintillation buffer and measured in a LSC instrument (Beckman, LS6000IC).

Example 13

PK/Tissue Distribution Studies of Isis 358346 in Balb/c Mice

In one embodiment of the invention, radiolabeled ($^3$H) Isis 358346, a peptide-PNA conjugate containing an activated disulfide, prepared as described herein in example 11 was examined for PK/tissue distribution, as described herein in example 12. Graphical analyses of the results of these experiments are shown in FIG. 4.

Example 14

Synthesis of uniform 2'-O-MOE oligonucleotide ISIS 386773 bearing a pyridyldisulfide functionality at the 5'-terminus.

The oligonucleotide ISIS 386773 and its unmodified control ISIS 364615 listed in the following table were synthesized and purified as described in Examples 2 and 3.

Example 15

Determination of the Plasma Protein Binding Capacity for ISIS 386773.

ISIS 386773 and its unmodified control ISIS 364615 were dissolved in PBS buffer and added to 100% mouse plasma to a final concentration ranging from 5 to 200 μM. The samples were incubated at 37° C. for ca. 30 min before the plasma proteins were quantitatively precipitated by the addition of 2 volumes of acetonitrile/ethanol (2:1). The samples were centrifuged in a bench top centrifuge at 13,000 rpm and the supernatant was analyzed by UV spectroscopy. The absorbance at 260 nm was recorded and used to calculate the amount of oligonucleotide in the supernatant as well as the amount oligonucleotide bound. FIG. 5 shows the plasma protein binding of the two oligonucleotides as a function of their plasma concentration. While the ISIS 386773 bearing the activated disulfide is significantly bound in the concentration range investigated, no binding could be detected for ISIS 364615, its unmodified control.

Example 16

Release of ISIS 386773 from Plasma Proteins Under Reductive Conditions.

The kinetics for the release of ISIS 386773 was measured after the addition of GSH in PBS to a final concentration of 5 mM to a sample of the oligonucleotide pre-bound to mouse plasma similar to Example 8. Aliquots were taken after 0, 15 30 and 60 min and plasma proteins were precipitated by the addition of 2 volumes of acetonitrile/ethanol (2:1). The samples were centrifuged in a bench top centrifuge at 13,000 rpm and the supernatant was analyzed by HPLC after the addition of a defined amount of a standard (PNA 6mer: H-CTATAG-NH$_2$). The amount of oligonucleotide released was determined by the ratio of analyte/standard. A non-GSH-treated sample and an aqueous non-plasma-containing sample were treated and analyzed identically and used to determine the 100%-bound and 100%-unbound reference levels, respectively. FIG. 6 shows the release kinetics of ISIS 386773 from plasma proteins after the addition of GSH.

Example 17

Kinetics of Plasma Protein Binding of ISIS 386773.

The kinetics for the binding of ISIS 386773 to plasma proteins was measured in 100% mouse plasma. Aliquots were taken after 1, 2, 4, 8, 16 and 32 min and plasma proteins were precipitated by the addition of 2 volumes of acetonitrile/ethanol (2:1). The samples were centrifuged in a bench top centrifuge at 13,000 rpm and the supernatant was analyzed by HPLC after the addition of a defined amount of a standard (PNA 6mer: H-CTATAG-NH$_2$) (Zorbax 300 SB C$_3$ column at 60° C.; eluent A: 0.1 M aq. ammonium acetate, B: CH$_3$CN; gradient: 0-60 in 30 min.). The amount of oligonucleotide released was determined by the ratio of analyte/standard. An aqueous non-plasma-containing sample was treated and analyzed identically and used to determine the 100%-unbound reference level. FIG. 7 shows the binding kinetics of ISIS 386773 to plasma proteins.

Although the invention has been described in detail with respect to various preferred embodiments it is not intended to be limited thereto, but rather those skilled in the art will recognize that variations and modifications may be made therein which are within the spirit of the invention and the scope of the appended claims.

All publications, patents, published patent applications, and other references mentioned herein are hereby incorporated by reference in their entirety.

| ISIS # | Sequence 5' to 3' | MW$_{calc}$ | MW$_{found}$ | SEQ ID NO: |
|---|---|---|---|---|
| 364615 | TGTCTCTGGTCCTTACTT | 6826.1 | 6826.1 | SEQ ID NO:11 |
| 386773 | Py-S—S—(CH$_2$)$_6$—O—P(O)$_2$-TGTCTCTGGTCCTTACTT | 7131.3 | 7131.2 | SEQ ID NO:12 |

We Claim:

1. A method of treating a subject with an antisense oligomer, the method comprising:
administering an antisense oligomer to a subject, wherein said antisense oligomer comprises an activated disulfide moiety selected from substituted or unsubstituted dithiopyridyl, substituted or unsubstituted dithiobenzothiazolyl, and substituted or unsubstituted dithiotetrazolyl, said antisense oligomer conjugated optionally with a bivalent linking group to said activated disulfide moiety, and wherein said activated disulfide moiety is capable of forming a disulfide bond with a plasma protein that is stable under plasma conditions and unstable under cellular conditions.

2. The method of claim 1, wherein the antisense oligomer is selected from an oligonucleotide, a peptide nucleic acid or a morpholino nucleic acid.

3. The method of claim 2, wherein the antisense oligomer is an oligonucleotide.

4. The method of claim 3, wherein the oligonucleotide comprises at least one 2'-modified nucleotide, wherein said 2'-modification is selected from halogen, alkoxy, substituted alkoxy, amino, or substituted amino.

5. The method of claim 3, wherein the oligonucleotide comprises at least one phosphorothioate internucleoside linkage.

6. The method of claim 3, wherein the oligonucleotide comprises at least one phosphodiester internucleoside linkage.

7. The method of claim 2, wherein the antisense oligomer is a peptide nucleic acid.

8. The method of claim 2, wherein the antisense oligomer is a double-stranded oligonucleotide.

9. The method of claim 8, wherein the double-stranded oligonucleotide comprises a first strand and a second strand.

10. The method of claim 9, wherein at least one nucleotide of the first or the second strand of the double-stranded oligonucleotide is 2'-modified nucleotide, wherein said 2' modification is selected from halogen, alkoxy, substituted alkoxy, amino, or substituted amino.

11. The method of claim 9, wherein at least one internucleoside linkage of the first or the second strand of the double-stranded oligonucleotide is a phophorothioate.

12. The method of claim 9, wherein at least one internucleoside linkage of the first or the second strand of the double-stranded oligonucleotide is a phosphodiester.

13. The method of claim 1, wherein said activated disulfide moiety comprises 2-pyridyl; 3-nitro-2-pyridyl, 5-nitro-2-pyridyl, 2-benzothiazolyl, N—($C_1$-$C_{12}$ alkyl)-2-pyridyl, N-oxide-2-pyridyl, or 1-methyl-2-1H-tetrazolyl.

14. The method of claim 1, wherein the bivalent linking group is a bivalent substituted or unsubstituted aliphatic group.

15. The method of claim 1, wherein the bivalent linking group is of the formula:
-$Q_1$-G-$Q_2$-, wherein
$Q_1$ and $Q_2$ are independently absent or selected from substituted or unsubstituted $C_1$-$C_{12}$ alkylene, substituted or unsubstituted alkarylene or —($CH_2$)$_m$—O—($CH_2$)$_p$—, wherein each m and p are, independently, an integer from 1 to about 10;
G is —NH—C(O)—, —C(O)—NH—, —NH—C(O)—NH—, —NH—C(S)—NH—, —NH—O—, NH—C(O)—O—, or —O—CH$_2$—C(O)—NH—.

16. The method of claim 14, wherein the bivalent linking group is selected from:

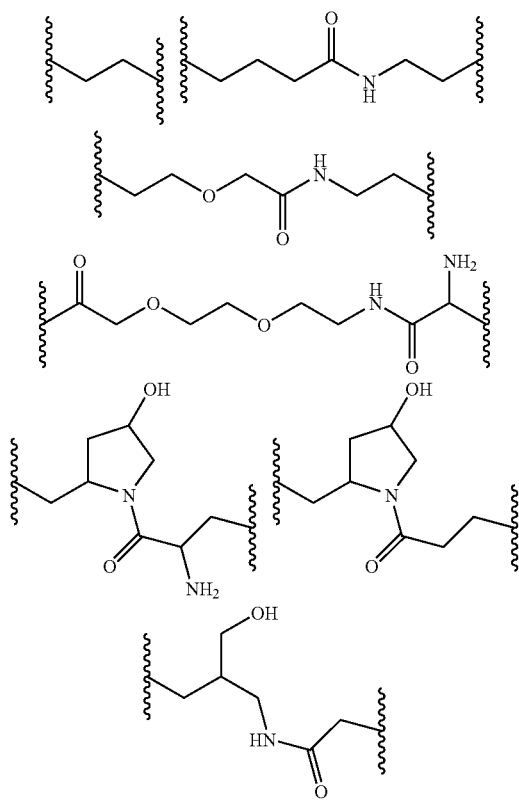

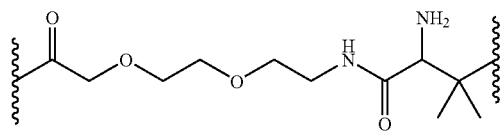

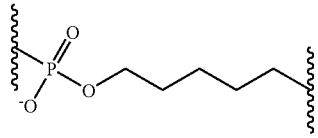

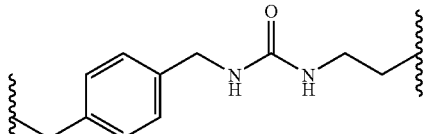

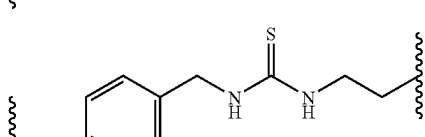

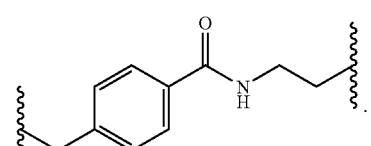

17. The method of claim 1, wherein the step of administering is intravenous, intraarterial, subcutaneous, intraperitoneal or intramuscular injection or infusion.

18. A method of heating a subject with an antisense oligomer, the method comprising:
selecting an antisense oligomer for forming a bio-reversible bond with a plasma protein in vivo, wherein said antisense oligomer is identified as capable of forming a bio-reversible bond with a plasma protein in vivo based on said antisense oligomer comprising an activated disulfide moiety capable of forming a disulfide bond with a plasma protein that is stable under plasma conditions and unstable under cellular conditions, and wherein said activated disulfide moiety selected from substituted or unsubstituted dithiopyridyl, substituted or unsubstituted dithiobenzothiazolyl, and substituted or unsubstituted dithiotetrazolyl, said antisense oligomer conjugated optionally with a bivalent linking group to said activated disulfide moiety and
administering said antisense oligomer to said subject.

* * * * *

UNITED STATES PATENT AND TRADEMARK OFFICE
CERTIFICATE OF CORRECTION

PATENT NO. : 7,713,944 B2　　　　　　　　　　　　　　　　　　　　　　　　Page 1 of 2
APPLICATION NO. : 11/251564
DATED : May 11, 2010
INVENTOR(S) : Garth A. Kinberger et al.

It is certified that error appears in the above-identified patent and that said Letters Patent is hereby corrected as shown below:

1) On the face of the patent, column 2, after (74) Attorney, Agent, or Firm please insert --Isis Pharmaceuticals Inc. Patent Dept.--;

2) Column 3, lines 23-24, please delete "2'modification" and insert therefor --2'-modification--;

3) Column 7, line 24, please delete "embodiments;" and insert therefor --embodiments,--;

4) Column 7, line 58, please delete "-Q," and insert therefor -- -$Q_1$--;

5) Column 9, line 15, please delete "3nitropyridyl," and insert therefor --3-nitropyridyl,--;

6) Column 25, line 2, please delete "The" and insert therefor --the--;

7) Column 25, line 8, please delete "Chem Bio Chem.," and insert therefor --ChemBioChem.,--;

8) Column 33, line 61, please delete "prefereably" and insert therefor --preferably--;

9) Column 36, lines 3-4, please delete "olignucleotide" and insert --oligonucleotide--;

10) Column 40, line 40, please delete "5" and insert therefor --S--;

11) Column 43, line 23, after "NS5B" please insert --.--;

12) Column 44, line 11, please delete "et. al.," and insert therefor --et al.,--;

13) Column 45, line 14, please delete "2' modification" and insert therefor --2'-modification--;

14) Column 47, line 31, please delete "mediumted" and insert therefor --mediated--;

15) Column 47, line 33, please delete "Peptides." and insert therefor --Peptides:--;

Signed and Sealed this

Ninth Day of November, 2010

David J. Kappos
*Director of the United States Patent and Trademark Office*

CERTIFICATE OF CORRECTION (continued)
U.S. Pat. No. 7,713,944 B2

16) Column 51, line 45, please delete "(3UTR)," and insert therefor --(3'UTR),--;

17) Column 52, line 23, please delete "more that" and insert therefor --more than--;

18) Column 76, claim 10, line 65-66, please delete "2' modification" and insert therefor --2'-modification--;

19) Column 77, claim 13, line 8, please delete "pyridyl;" to --pyridyl,--;

20) Column 78, claim 18, line 38, please delete "heating" to --treating--;

21) Column 78, claim 18, line 55, after "moiety" please insert --;--.